(12) United States Patent
Oleson et al.

(10) Patent No.: US 10,021,188 B2
(45) Date of Patent: *Jul. 10, 2018

(54) ATHLETIC PERFORMANCE MONITORING WITH DYNAMIC PROXIMITY PAIRING

(71) Applicant: Under Armour, Inc., Baltimore, MD (US)

(72) Inventors: Mark A. Oleson, Baltimore, MD (US); F. Grant Kovach, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 701 days.

This patent is subject to a terminal disclaimer.

(21) Appl. No.: 14/477,557

(22) Filed: Sep. 4, 2014

(65) Prior Publication Data
US 2015/0061891 A1    Mar. 5, 2015

Related U.S. Application Data

(63) Continuation-in-part of application No. 14/175,457, filed on Feb. 7, 2014, now Pat. No. 9,621,684.

(60) Provisional application No. 61/762,175, filed on Feb. 7, 2013.

(51) Int. Cl.
| | |
|---|---|
| G06F 15/16 | (2006.01) |
| H04L 29/08 | (2006.01) |
| H04W 4/80 | (2018.01) |
| H04W 4/00 | (2018.01) |
| H04W 4/02 | (2018.01) |
| G06F 19/00 | (2018.01) |

(52) U.S. Cl.
CPC ............. *H04L 67/12* (2013.01); *H04W 4/008* (2013.01); *H04W 4/02* (2013.01); *H04W 4/80* (2018.02); *G06F 19/3481* (2013.01)

(58) Field of Classification Search
CPC .... G06F 19/3481; H04L 67/12; H04W 4/008; H04W 4/02
USPC ................................. 709/201, 202, 208, 216
See application file for complete search history.

(56) References Cited

U.S. PATENT DOCUMENTS

| | | |
|---|---|---|
| 5,440,300 A | 8/1995 | Spillman, Jr. |
| 5,454,376 A | 10/1995 | Stephens |
| 5,456,262 A | 10/1995 | Birnbaum |
| (Continued) | | |

OTHER PUBLICATIONS

Gamin Ltd., "Garmin ANT + in the gym", captured on Mar. 27, 2009 by archive.org/web/ from http://www8.garmin.com/intosports/antplus.html.*

*Primary Examiner* — Davoud Zand
(74) *Attorney, Agent, or Firm* — Maginot, Moore & Beck LLP

(57) ABSTRACT

A method of monitoring biometric data for an individual includes sensing a biometric parameter of the individual with a sensor carried by the individual. The method further comprises detecting that the individual has moved within a predetermined range of a fixed display device, and then wirelessly transmitting the sensed biometric parameter to a receiver associated with the fixed display device after the detection that the individual has moved within the predetermined range. The sensed biometric parameter of the individual is then displayed on the fixed display device. Thereafter, the fixed display device detects that the individual has moved outside of the predetermined range and removes the sensed biometric parameter of the individual from the fixed display device.

20 Claims, 15 Drawing Sheets

(56) References Cited

U.S. PATENT DOCUMENTS

| | | | |
|---|---|---|---|
| 5,891,042 A | 4/1999 | Sham | |
| 6,002,427 A * | 12/1999 | Kipust | G06F 21/552 340/571 |
| 6,159,130 A | 12/2000 | Torvinen | |
| 6,254,548 B1 | 7/2001 | Ishikawa | |
| 6,605,038 B1 | 8/2003 | Teller | |
| 6,736,759 B1 | 5/2004 | Stubbs | |
| 6,755,795 B2 | 6/2004 | Marmaropoulos | |
| 6,808,472 B1 | 10/2004 | Hickman | |
| 6,971,072 B1 * | 11/2005 | Stein | G06F 3/011 382/267 |
| 6,991,586 B2 | 1/2006 | Lapcevic | |
| 7,173,437 B2 | 2/2007 | Hervieux | |
| 7,191,013 B1 | 3/2007 | Miranda | |
| 7,254,516 B2 | 8/2007 | Case, Jr. | |
| 7,454,002 B1 | 11/2008 | Gardner | |
| 7,603,255 B2 | 10/2009 | Case, Jr. | |
| 7,607,243 B2 | 10/2009 | Berner, Jr. | |
| 7,658,716 B2 | 2/2010 | Banet | |
| 7,670,263 B2 | 3/2010 | Ellis | |
| 7,811,201 B1 | 10/2010 | Mikan | |
| 8,015,732 B2 | 9/2011 | Berner, Jr. | |
| 8,073,707 B2 | 12/2011 | Teller | |
| 8,105,208 B2 | 1/2012 | Oleson | |
| 8,460,001 B1 | 6/2013 | Chuang | |
| 8,499,476 B2 | 8/2013 | Berner, Jr. | |
| 8,595,810 B1 * | 11/2013 | Ben Ayed | H04L 63/0815 713/168 |
| 8,857,078 B2 | 10/2014 | Berner, Jr. | |
| 8,907,782 B2 * | 12/2014 | Baker | H04W 76/38 340/539.12 |
| 9,188,963 B2 | 11/2015 | Gray | |
| 9,204,797 B2 | 12/2015 | Gray | |
| 9,451,881 B2 | 9/2016 | Gray | |
| 2002/0109600 A1 | 8/2002 | Mault | |
| 2005/0195094 A1 | 9/2005 | White | |
| 2005/0267550 A1 | 12/2005 | Hess | |
| 2006/0136173 A1 * | 6/2006 | Case, Jr. | A63B 24/00 702/182 |
| 2006/0200204 A1 * | 9/2006 | Daum | A61N 1/365 607/19 |
| 2007/0033069 A1 | 2/2007 | Rao | |
| 2007/0106132 A1 | 5/2007 | Elhag | |
| 2007/0159926 A1 | 7/2007 | Prstojevich | |
| 2007/0179359 A1 | 8/2007 | Goodwin | |
| 2007/0219059 A1 | 9/2007 | Schwartz | |
| 2007/0296571 A1 | 12/2007 | Kolen | |
| 2008/0094228 A1 | 4/2008 | Welch | |
| 2008/0177994 A1 * | 7/2008 | Mayer | G06F 9/4418 713/2 |
| 2008/0200310 A1 | 8/2008 | Tagliabue | |
| 2008/0214903 A1 | 9/2008 | Orbach | |
| 2008/0252445 A1 | 10/2008 | Kolen | |
| 2008/0287062 A1 * | 11/2008 | Claus | H04W 12/02 455/41.2 |
| 2008/0319282 A1 | 12/2008 | Tran | |
| 2009/0232361 A1 * | 9/2009 | Miller | G06K 9/6293 382/115 |
| 2009/0292179 A1 | 11/2009 | Jampala | |
| 2010/0059561 A1 | 3/2010 | Ellis | |
| 2010/0185398 A1 | 7/2010 | Berns | |
| 2011/0125866 A1 * | 5/2011 | Williams | G06F 19/3418 709/217 |
| 2011/0137213 A1 | 6/2011 | Caulfield | |
| 2012/0041767 A1 | 2/2012 | Hoffman | |
| 2012/0109013 A1 | 5/2012 | Everett | |
| 2012/0167124 A1 * | 6/2012 | Abdeljaoued | H04H 60/45 725/11 |
| 2012/0219036 A1 | 8/2012 | Teague | |
| 2012/0320736 A1 * | 12/2012 | Hillier | H04M 3/2263 370/218 |
| 2013/0032634 A1 | 2/2013 | McKirdy | |
| 2013/0090942 A1 * | 4/2013 | Robinson | G06Q 50/22 705/2 |
| 2013/0298208 A1 * | 11/2013 | Ayed | G06F 21/00 726/6 |
| 2014/0002444 A1 * | 1/2014 | Bennett | G06F 3/012 345/419 |
| 2014/0330144 A1 * | 11/2014 | Dugan | A61B 5/0002 600/508 |

* cited by examiner

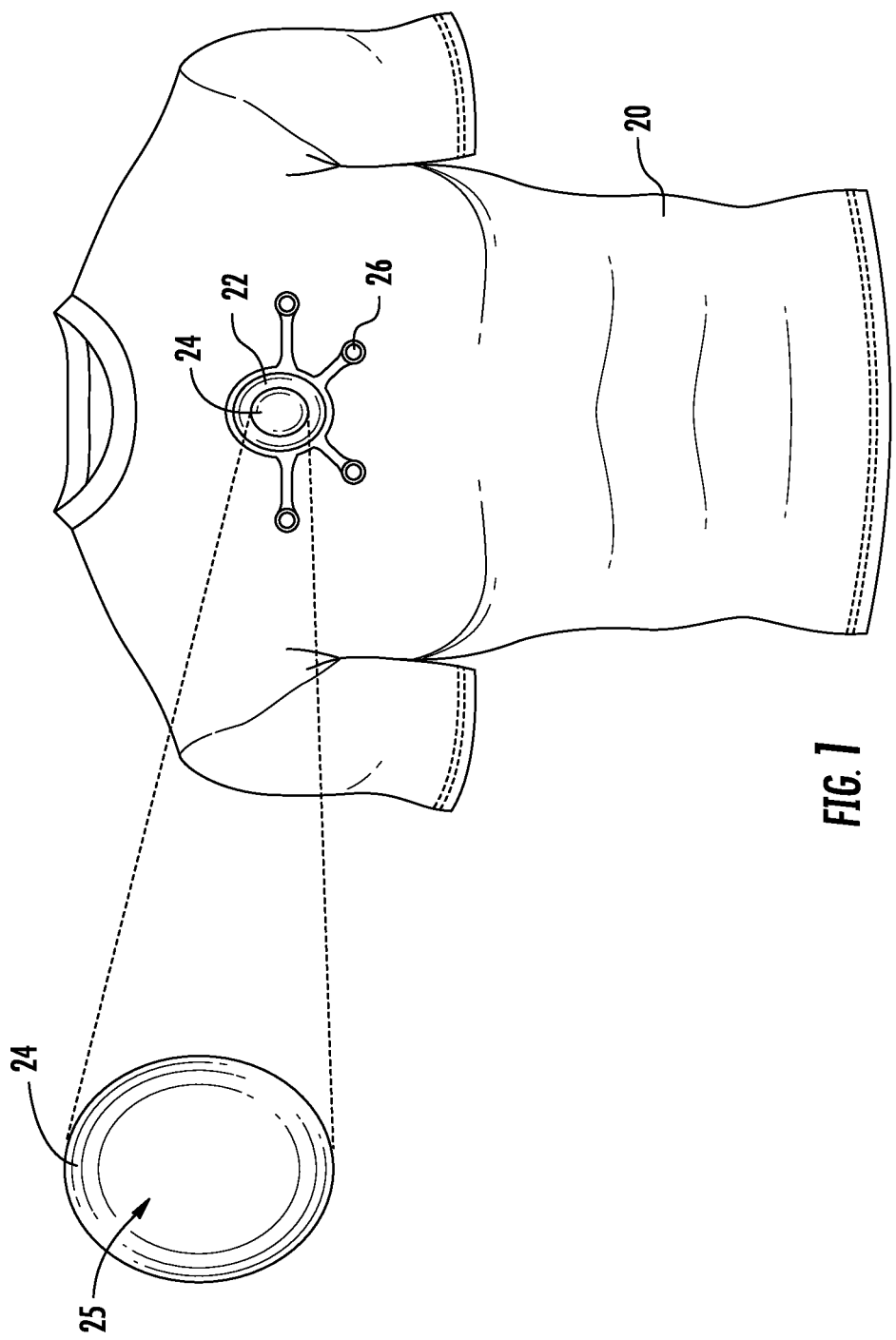

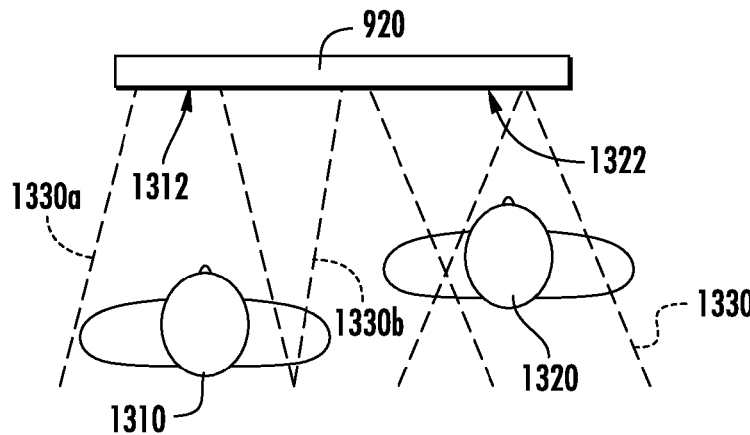
FIG. 13
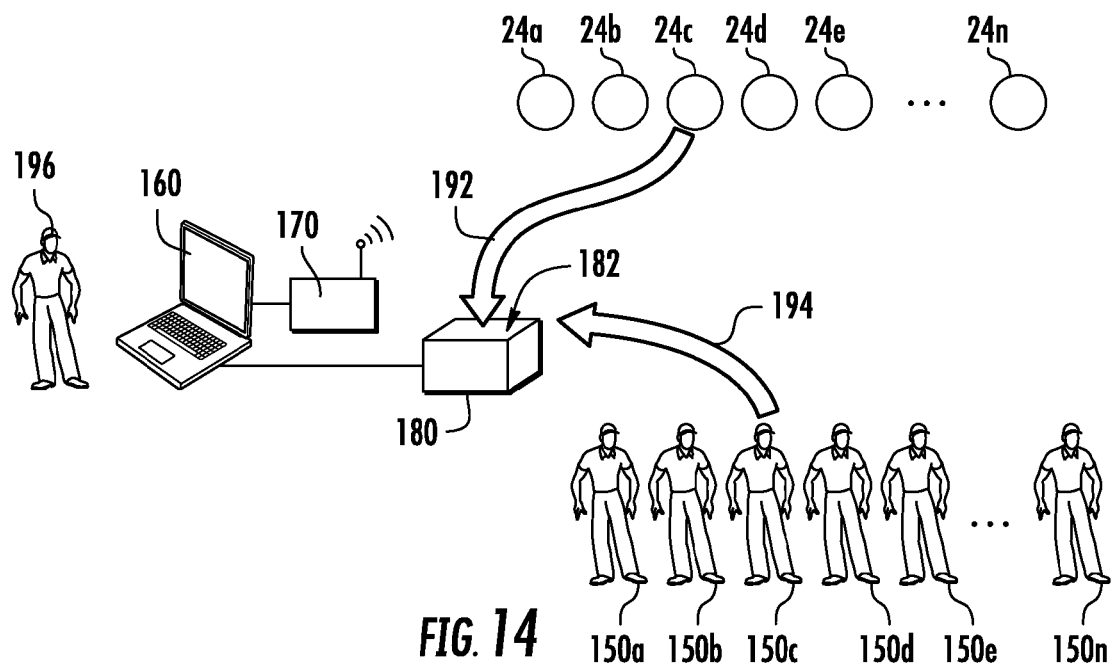
FIG. 14
| NAME | ID # |
|---|---|
| Joe Flacco | A5678C |
| Peyton Manning | A1234B |
| Andrew Luck | ———— |
FIG. 15

ATHLETIC PERFORMANCE MONITORING WITH DYNAMIC PROXIMITY PAIRING

CROSS-REFERENCE TO RELATED APPLICATIONS

This application is a continuation-in-part of U.S. patent application Ser. No. 14/175,457, filed Feb. 7, 2014, which claims priority from provisional patent application No. 61/762,175, filed Feb. 7, 2013.

FIELD

This application relates to physiological data and performance monitoring, and more particularly to systems for sensing, processing and displaying biometric data.

BACKGROUND

Athletes and their trainers often keep track of the progress and conditioning of the athlete. Many computerized systems exist which collect biometric data from an athlete during training and subsequently process and display such information for use by the athlete or the trainer. Recently, such systems have become available where the sensor designed to collect the biometric data is incorporated into an athletic garment worn by the athlete. An example of such a system is disclosed in U.S. Patent Publication No. 2010/0185398.

With many existing athletic monitoring systems, biometric data for an athlete is collected by a sensing device during a training session. The biometric data collected during the training session is stored in the memory of a computer that is carried by the athlete. For example, an athlete may wear a heart rate monitor during a training session, and data from the heart rate monitor may be transmitted to the memory of a handheld personal computer carried by the athlete (e.g., a wristwatch, smartphone or other handheld personal computer in wired or wireless communication with the sensor, which handheld personal computers may be referred to herein as "handheld devices"). The handheld personal computer may process the data locally or may transmit data to a remote location for processing and/or storage. For example, data transmitted to the handheld personal computer may be transmitted over the cellular telephone network to an internet server or other network computer for further processing (e.g., processing within "the cloud").

With existing athletic monitoring systems, biometric data collected by a sensing device is often displayed on the handheld device for viewing by the athlete. However, in some environments, the athlete may wish to view biometric data collected by the sensing device on a larger display instead of the small screen associated with a handheld device. There may be several reasons for this. For example, the data displayed on a handheld device may be small and difficult to read. Furthermore, the athlete may have forgotten or decided not to carry a handheld device during the workout. In these situations, obtaining biometric data collected from the sensing device is not possible until the athlete completes the workout or retrieves the handheld device.

In view of the foregoing, it would be advantageous to provide the athlete with the opportunity to view biometric data during a training session or other sporting event without the use of a handheld device. It would be particularly advantageous if the system were convenient to use for the athlete while also being relatively easy and inexpensive to implement.

SUMMARY

In at least one embodiment, a method of monitoring biometric data for an individual includes sensing a biometric parameter of the individual with a sensor carried by the individual. The method further includes detecting that the individual has moved within a predetermined range of a fixed display device, and wirelessly transmitting the sensed biometric parameter to a receiver associated with the fixed display device after the detection that the individual has moved within the predetermined range. The method further includes displaying the sensed biometric parameter of the individual on the fixed display device. In addition, the method includes detecting that the individual has moved outside of the predetermined range, and removing the sensed biometric parameter of the individual from the fixed display device after detecting that the individual has moved outside of the predetermined range.

In another embodiment, an arrangement for monitoring biometric data for an individual includes a sensor and a fixed display device. The sensor is configured to sense a biometric parameter of an individual carrying the sensor. The fixed display device configured to (i) determine that a target is within a predetermined range of the fixed display device, (ii) receive a wireless transmission including the sensed biometric parameter, (iii) display the sensed biometric parameter on a display screen when the target is within the predetermined range, and (iv) remove the sensed biometric parameter from the display screen after the target is outside of the predetermined range.

BRIEF DESCRIPTION OF THE DRAWINGS

FIG. 1 is a front view of an athletic garment with a sensor module configured for use in association with a system for monitoring athletic performance;

FIG. 13 is a top view of one of the fixed display devices of FIG. 9 configured to display biometric data for a plurality of targets.

FIG. 14 shows a diagram of a plurality of sensor modules to be paired with members of a team using a registration device; and FIG. 15 shows an exemplary computer display including a list of the members of the team of FIG. 14 and the associated identification numbers for the sensor devices associated with the team members.

DESCRIPTION

Figure 2A:
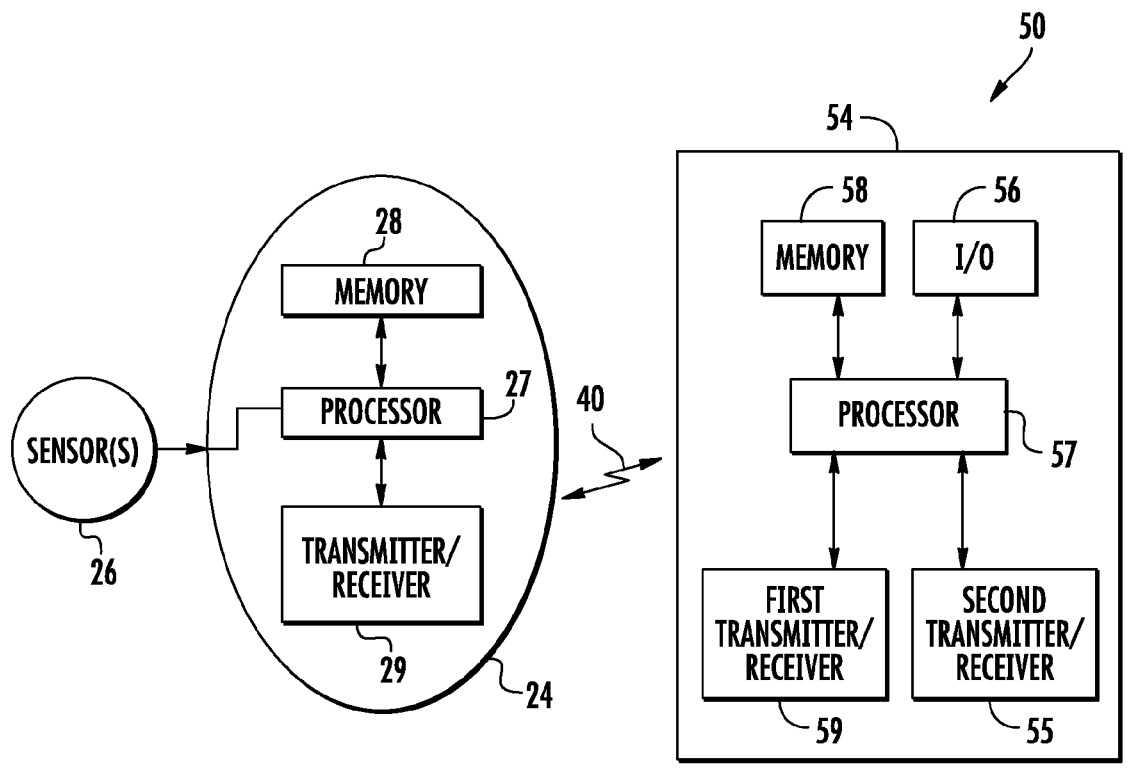
FIG. 2A is a block diagram of an electronic components arrangement in the sensor module of FIG. 1 and a smartphone in communications with the sensor module.

Referring to FIG. 1, there is shown a diagrammatic view of an exemplary embodiment of a system for monitoring an athlete's performance as the athlete participates in a sporting event. It will be understood that the embodiment discussed herein may be implemented in many alternate forms and variations. Furthermore, the word "sporting event" as used herein refers to any organized or unorganized event where a human participates in a team or individual competition, or a team or individual training session or activity. Examples of "sporting events" include both professional and amateur sports competitions (whether team or individual), team or individual practice sessions to further develop physical skills or prepare for a competition, and/or any team or individual physical workout, physical exercise, athletic conditioning or training session (whether or not in preparation for a competition), or entertainment activity involving physical exertion. The word "sporting venue" as used herein refers to a gym or other building, field, street, course, trail, stadium, facility, or any other location where a sporting event occurs. The word "athlete" as used herein refers to any human participating in a sporting event. The word "garment" as used herein refers to shirts, shorts, pants, socks, shoes, watches, wristbands, chest bands, head bands, hats, headgear, or any other clothing, footwear, accessory or equipment worn on the human body. Furthermore, the term "hand held computing device" as used herein refers to any of various computing devices that are relatively small and portable, including smartphones, wrist watches, tablet computers, laptop computers, and other computerized personal assistant devices.

With reference now to FIG. 1, a garment 20 is shown in the form of a shirt. The shirt includes a receptacle 22 configured to hold a sensor module 24. At least one sensor 26 is positioned on the shirt or on the athlete wearing the shirt. The sensor 26 is configured to sense biometric data from the athlete wearing the shirt and deliver the sensed biometric data to a transceiver in the sensor module 24. The transceiver is configured to deliver the sensed biometric data to a handheld computing device 50 (see FIG. 2A) in communications with the sensor module 24.

With continued reference to FIG. 1, the receptacle 22 on the shirt may be provided in any of numerous forms, including the embodiments described in U.S. patent application Ser. No. 12/692,528 filed Jan. 22, 2010, and U.S. patent application Ser. No. 13/629,207 filed Sep. 27, 2012, the contents of which are incorporated herein by reference in their entirety. The receptacle 22 is configured to secure the sensor module 24 in place on the garment 20 when it is worn by the user. In at least one embodiment, the receptacle 22 secures the sensor module 24 to the garment 20 in a releasable fashion such that the sensor module 24 may be removed from the garment by the user without damaging the receptacle or the garment. However, in another alternative embodiment, the sensor module 24 may be secured on the garment 20 in a permanent fashion.

As shown in FIG. 2A, the sensor module 24 includes electronic circuitry comprising a processor 27, a memory 28, and a transceiver 29 protected within a durable shell 25 (the electronic circuitry for such electronic devices is known to those of ordinary skill in the art and is not shown in detail in the figures). The processor 27 may be any of various processors as will be recognized by those of ordinary skill in the art, such as various processors sold by Intel Corporation or AMD. The processor 27 is configured to receive biometric data signals from the sensors 26 provided on the garment 20 or otherwise carried by the athlete. The processor 27 is connected to both the memory 28 and the transceiver 29, and may deliver received sensor data to either the memory 28 or the transceiver 29. Additionally, the processor 27 may perform some processing on the received sensor data prior to delivery to the memory 28 or the transceiver 29. For example, the processor 27 may filter the received biometric data from the sensor 26 prior to delivery of the data to the memory 28. Additionally, the processor 27 may associate the received biometric data with additional information for storage in the memory, such as association of the received biometric data with a particular time and/or sporting event.

The memory 28 is configured to store information, and particularly data that may be retrieved or manipulated by the processor 27, along with software for execution by the processor 27. The memory 28 may be of any type capable of storing information accessible by the processor, such as a memory card, ROM, RAM, write-capable, read-only memories, or other computer-readable medium. The data may be stored in the memory 28 in a relational database as a table having a plurality of different fields and records, XML documents, or flat files. The data may also be formatted in any computer-readable format such as, but not limited to, binary values, ASCII or Unicode.

The transceiver 29 is an rf transmitter and receiver configured to transmit and receive communications signals over a short range using a wireless communications technology standard, such as Bluetooth®. Such transceivers are well known and will be recognized by those of ordinary skill in the art. The sensor module 24 also includes a battery (not shown) configured to power the electronics devices within the sensor module 24. In at least one embodiment, the battery of the sensor module 24 is a rechargeable battery. In this embodiment, the sensor module 24 may be placed in a battery charger configured for use with the sensor module in order to recharge the battery.

The electronics for the sensor module 24, including the processor 27, the memory 28, and the transceiver 29, are housed within the shell 25 to keep the electronics within the sensor module safe. Accordingly, the shell 25 may be comprised of a polymer, or fabric material capable of absorbing impacts without damage to the electronics embedded in the shell. Electrical contacts may be provided on the sensor module 24 to allow the module 24, and particularly the processor 27, to receive biometric data signals or other data signals delivered from the sensors 26 through a wire. Alternatively the electronics for the sensor module 24 may be completely enclosed in the shell material and receive the signals from the sensors 26 via a wireless connection to the transceiver 29. Because of the overall shape of the shell 25 of the sensor module 24, the terms "bug" and "puck" may also be used to refer to the sensor module 24. However, the sensor module may be any of various sizes, shapes and configurations, as will be recognized by those of ordinary skill in the art.

The sensors 26 positioned on the garment 20 include any of numerous sensor types, including biometric sensors, performance signals, environmental sensors, positional sensors, or other types of sensors. Biometric sensors include any of various sensors that may be used to sense various physiological conditions of the athlete and deliver signals related to such conditions. For example, the biometric sensors 26 may include heart rate sensors, breathing rate sensors, hydration sensors, body temperature sensors, muscle fatigue sensors and numerous other sensors configured to detect various physiological conditions. The biometric sensors may be provided in any of various different configurations and arrangements as will be recognized by those of skill in the art. Exemplary performance sensors include accelerometers, timers, or other sensors configured to collect athletic performance data such as speed, acceleration, jump height, or any of various other athletic performance parameters as will be recognized by those of ordinary skill in the art. Examples of environmental/positional sensors include GPS receivers, accelerometers, air temperature sensors, clocks, or hygrometers. The sensors 26 may be incorporated directly into the garment, housed within the sensor module 24, or may otherwise be worn or held by the athlete during the sporting event. For example, a heart rate sensor may be embedded in a shirt worn by the athlete or may be worn on a band encircling the athlete's chest. A GPS receiver may be provided directly in the sensor module 24, may be fastened to a shirt, or may be provided on a portable media player or telephone clipped to the athlete's waistband. Of course, these are but a few examples of sensors and configurations of sensors that may be used by the athlete in association with the bug. When the sensors are incorporated into the garment 20, they may include electrical connections that lead directly to the receptacle, allowing the sensor module 24 plugged into the receptacle to receive signals from the sensors 26. Alternatively, the garment 20 may include an electrical connector adapted for connection to other sensors that are not incorporated into the garment. In yet another embodiment, the sensors may each include an associated transmitter that transmits the sensor signal to the sensor module 24 in a wireless manner. In at least one embodiment, data from the sensors 26 may also be transmitted from the bug to the wireless telephony network.

With continued reference to FIG. 2A, in at least one embodiment, the handheld computing device 50 is a smartphone 54. The smartphone 54 includes an input/output interface 56, a processor 57, a memory 58, a first transceiver 59 and a second transceiver 55. While a smartphone 54 has been shown as the handheld computing device 50 in FIG. 2A, it will be appreciated that the handheld computing device 50 may be provided in other forms in addition to or in lieu of the smartphone 54. For example, the handheld computing device 50 may be provided in the form of a watch, tablet computer, laptop computer, or other computing device. In yet other embodiments, the computing device may not be a handheld computing device, but may be a stationary computing device, such as a personal computer. As will be recognized by those of ordinary skill in the art, if the computing device is a handheld computing device 50, different devices may have different functionality. For example, if the handheld computing device 50 is a watch, it may include much of the same functionality and components as the smartphone 54, but may not include all the same functionality or components, such as a different display or different software applications.

The I/O interface 56 of the smartphone 54 includes software and hardware configured to facilitate communications with the athlete. The hardware may include a touchscreen display for visual communications and speakers for audio communications. The touchscreen display allows the user to see data presented on the screen and input data into the handheld computing device 50 via a keyboard on the touchscreen.

The processor 57 of the smartphone 54 may be any of various processors as will be recognized by those of ordinary skill in the art. The processor 57 is connected to the I/O interface 56, the memory 58, the first transceiver 59, and the second transceiver 55, and may deliver data to and receive data from each of these components.

The memory 58 is configured to store information, and particularly apps and other software for execution by the processor 57. The memory 58 may be of any type capable of storing information accessible by the processor, such as a memory card, ROM, RAM, write-capable, read-only memories, or other computer-readable medium.

The first transceiver 59 is an rf transmitter and receiver configured to transmit and receive communications signals over a short range using a wireless communications technology, such as Bluetooth®, using any of various protocols, such as TCP/IP. Such transceivers are well known and will be recognized by those of ordinary skill in the art. The smartphone 54 also includes a battery (not shown) configured to power the electronic components within the smartphone 54.

The second transceiver 55 is configured to allow the smartphone 54 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

The second transceiver 55 of the smartphone 54 is configured to transmit data to the internet/cloud using a wireless telephony network, as illustrated by reference numeral 60.

This wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements. The wireless telephony network, in turn, is connected to the internet/cloud 66 via the hardware of the particular mobile service provider.

Figure 3:
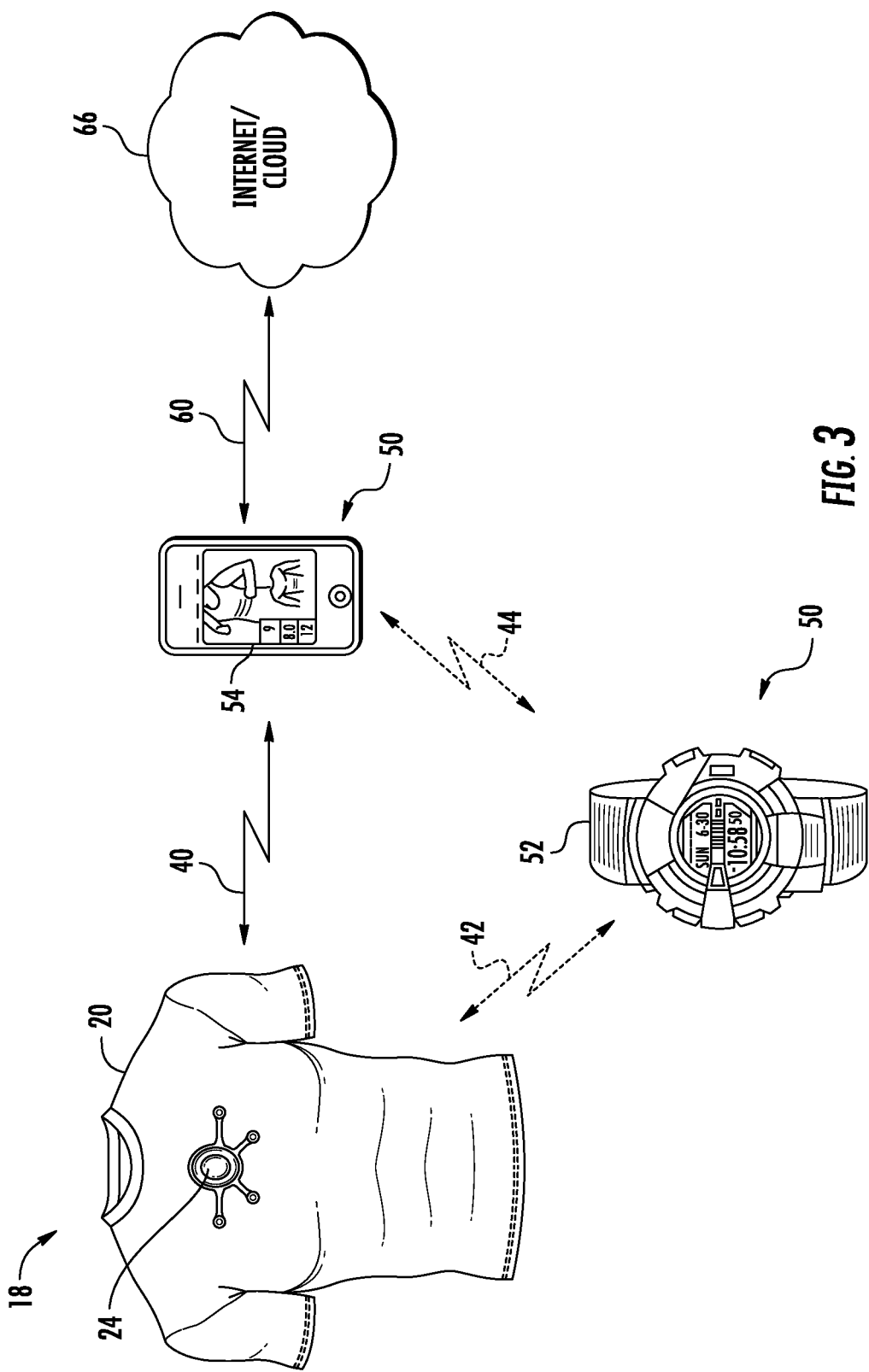
FIG. 3 is a diagrammatic view of a communications network for the system of monitoring athletic performance of FIG. 1, the communications network having a plurality of devices in wireless communication, including the sensor module, the smartphone, and a watch.

With reference now to FIG. 3, raw biometric data received by the smartphone 54 may be processed by the handheld computing device 50 or delivered to the cloud 66 for further processing. The processing to be performed may depend on various factors including the type of data received and different subscriptions of the user/athlete. Typical processing might relate to the athlete's current performance level, trends, history, training state, etc. For example, if heart rate data for the athlete is collected, the processing server may plot the data on a graph showing the athlete's heart rate during the entire sporting event. As another example, if body temperature data is collected, the processor may calculate an average body temperature during the sporting event and display the average body temperature on a historical chart of average body temperatures for other sporting events. If GPS data is collected, the speed of the athlete may be calculated over different time periods. Furthermore, the biometric data may be processed into different forms and formats, depending on the particular device that will ultimately be used to view the processed data. For example, the data may be processed into a first format that will allow it to be viewed on a watch and into a second format that will allow it to be viewed on the monitor of a personal computer. While these are but a few examples of how the raw data may be processed, those of skill in the art will recognize that nearly countless other possibilities exist for how the data received from the garment 20 will be processed for subsequent viewing and analysis.

As indicated by arrows 40, 44 and 60 in FIG. 3, after the raw data is processed by the smartphone 54 or within the cloud 66, the processed data may be displayed at one of several viewing devices, such as the smartphone 54 or the watch 52. Such devices may include screens for viewing the processed biometric data, speakers or other audible output devices for sounding information about the processed biometric data, vibration devices and/or other output devices for transmitting information related to the processed data.

In operation, when an athlete wearing the garment 20 participates in a sporting event, biometric data is delivered to the sensor module 24 from the sensors 26 worn by the athlete. As represented by arrows 40 and 42, and 44 in FIG. 3, the sensor module 24 is configured to transmit an rf signal representative of the biometric data received by the sensor module to at least one handheld computing device 50, such as the smartphone 54. In addition, the biometric data may also be transmitted to additional handheld computing devices, such as the watch 52, where the data may be conveniently displayed for the user during a sporting event. This transmission from the sensor module 24 to the handheld computing device occurs automatically without the athlete needing to prompt the transmission. Because the transmissions are automatic, some mechanism may be used to turn on the transmitter 29 of the sensor module 24 or otherwise indicate that automatic transmissions should begin. For example, in one embodiment, an on/off switch is provided on the sensor module 24 that allows the athlete to begin automatic transmissions of data from the sensor module 24. In another embodiment, the sensor module 24 may be configured to begin transmissions once it starts receiving biometric data signals from a sensor worn by the athlete. In yet another embodiment, the sensor module 24 may only begin transmissions once the data signals received from the sensor indicate that an athletic event has started (e.g., increased heart rate or temperature). In yet another embodiment, the sensor module may only begin transmissions once a confirmation signal has been received from the handheld computing device.

In addition to automatic transmissions from the sensor module 24, it will also be noted that the transmission of data from the sensor module 24 to the handheld personal computer 50 typically occur in real-time, i.e., at the same time the athlete participates in the sporting event. In one embodiment, the sensor module 24 transmits biometric data immediately upon receipt of a signal from the sensor worn by the athlete. However, in other embodiments, the sensor module 24 may be configured to conserve power by only transmitting data in a periodic fashion, such as once every second, once every ten seconds, once every thirty seconds, etc. In these embodiments, the memory 28 in the sensor module 24 may be configured to store a limited amount of data taken over a short period of time and then transmit that data and associated time period information in a single transmission. The smartphone 54, in turn, is configured to regularly and automatically transmit data to a wireless telephony network as the athlete participates in the sporting event.

User Feedback Based on Processed Heart Rate Data from Sensor

In at least one embodiment, the handheld computing device 50 (e.g., smartphone 54) is configured to determine the accuracy of heart rate information collected and assist the user in making the collected heart rate information more accurate. Heart rate data is collected from a sensor on the sensor module 24, may be filtered using a standard bandpass filter, and is processed to the handheld computing device 50 for processing. The heart rate data may include (i) unfiltered beat-to-beat information, including the time between heart beats and the heart rate variability (i.e., the variation in the beat-to-beat interval), and (ii) filtered heart rate data (such as the filtered measurement of beats per minute), as well as other information (e.g., ECG, etc.). In at least one embodiment, the beat-to-beat data is extrapolated over a minute, and a determination is made concerning the amount of noise in the data. The amount of noise present in the heart rate information may be determined in various ways such as an analysis of the signal-to-noise ratio in the unfiltered beat-to-beat information. As another example, noise present in the heart rate information may be determined based on a combination of the unfiltered beat-to-beat information, as well as the filtered heart rate data. For example, if the unfiltered beat-to-beat information is not consistent with the filtered heart rate data, or within a predetermined tolerance, it can be determined that an unacceptable amount of noise is present in collection of the heart rate data, and thus the heart rate data collected during the sporting event may be inaccurate. As yet another example, the noise in the heart rate information may be determined by analyzing the heart rate variability collected from the unfiltered beat to beat information and, if the time between beats varies widely, determining that inaccurate heart rate data is being collected.

When the system detects that the collected heart rate data is inaccurate, the system urges the user to take steps to make the heart rate data more accurate. Inaccurate heart rate data is often (and most likely) the result of a faulty sensor arrangement on the user's body (e.g., improper placement of the sensor on the body, or additional moisture needed on the sensor electrodes). Thus, when a determination is made that the heart rate data is inaccurate, a message is displayed on the smartphone 54 informing the user that the system is having difficulty collecting heart rate information and providing instructions for adjustment of the heart rate sensor in an attempt to obtain more accurate heart rate data. Examples of instructions provided to the user may include an instruction to "adjust your strap", "moisten the electrodes on the sensor", or showing an illustration of proper sensor placement on the body. An additional example of an instruction to the user includes asking the user to stand still for a minute, thus allowing the system to determine if the noisy heart rate signal is simply a result of a high activity level by the user or an improper sensor arrangement or improper sensor functionality. These instructions may be provided on a display screen and/or audibly with a voice message or warning tones. If appropriate actions by the user do not result in correction of the collected heart rate data, a message may be displayed or otherwise communicated instructing the user to take his or her sensor module to a service center for further analysis.

Data Transmission Based on Signal Strength

In certain circumstances, the sensor module 24 is further configured to temporarily suspend data transmissions when communications between the sensor module 24 and the handheld computing device are disrupted. In these situations, the sensor module 24 temporarily saves the data that would normally be transmitted to the handheld computing device 50 in real time to the internal memory 28 on the sensor module 24. In at least one embodiment, the internal memory 28 on the sensor module 24 is configured to retain ten hours or more of biometric data received from the sensor. However, it will be recognized that the memory 28 may be configured to retain any of various amounts of data.

In at least one embodiment, the processor 27 of the sensor module 24 determines that communications have been disrupted when a signal strength for communications with the smartphone 54 do not meet a certain threshold. When the sensor module 24 suspends transmission of data to the smartphone 54, the sensor module saves the data in internal memory 28. This data is saved in the internal memory 28 until a later time when an acceptable signal strength is achieved between the sensor module 24 and the smartphone 54. "Signal strength" generally refers to a received signal level or field strength. It is often expressed in dB-microvolts per meter (dBμV/m) or in decibels above a reference level of one milliwatt (dBm). Various metrics have been established to provide an indication of signal strength. For example, Bluetooth® uses the received signal strength indicator (RSSI) measurement to provide a measurement of the power level of an rf signal received by an antenna. Thus, in the embodiment disclosed herein, the transmitter/receiver 29 provides an RSSI number to the processor 27 to provide an indication of the signal strength between the sensor module 24 and the smartphone 54. The higher the RSSI number (or less negative in some embodiments), the stronger the signal.

Figure 4:
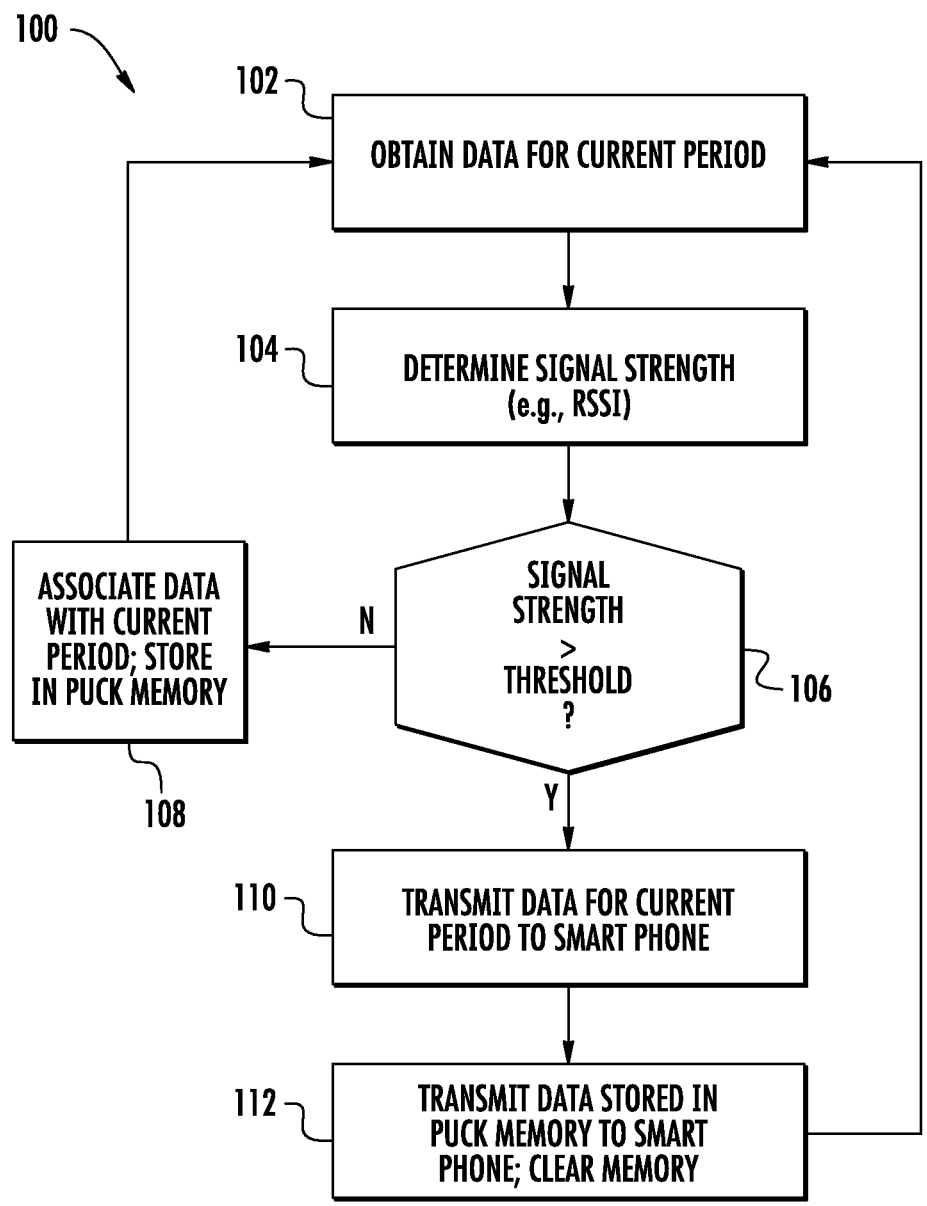
FIG. 4 is a flowchart of a method of storing and transmitting data using the communications network of FIG. 3.

With reference now to FIG. 4, a method 100 is disclosed for managing data transmissions from the sensor module 24 to the smartphone 54. The method begins in block 102 when the processor 27 obtains data for a current time period from the sensors 26. As discussed above, the data may be any of various types of biometric data such as heart rate data, accelerometry data, or temperature. Accordingly, examples of collected data may be a heart rate measured in beats per second, an angle of inclination, or body temperature. The time period may be any of various intervals of time, such as one second, five seconds, thirty seconds, or any other period of time deemed appropriate for the collection of the desired biometric data.

In block 104 the processor 27 determines a current signal strength for a signal received from the sensor module 24. The determination of signal strength may be according to one of various known metrics, such as RSSI. In general, RSSI may be used to determine an amount of radio energy in a channel. The processor 27 in the sensor module 24 observes an RSSI value indicative of a measured signal strength provided from the communications card of the transceiver 29 or other wireless network monitoring tool. Different wireless network monitoring tools will provide different RSSI values. For example, one communications card may provide RSSI values between 0 to 100, while another communications card may provide RSSI values between 0 to 127. Because there is no standardized relationship of any particular physical parameter to the RSSI reading, different card vendors provide their own accuracy, granularity, and range for the actual power (typically measured as mW or dBm) and their range of RSSI values (e.g., from 0 to RSSI_Max).

A threshold value is pre-determined as an acceptable for data transmission between the sensor module 24 and the smartphone 54. This threshold value will generally depend on the range of RSSI values associated with the transceiver 27, as described above. Accordingly, in block 106, the processor determines whether the signal strength determined in block 104 is greater than the threshold value.

If the determined signal strength is less than the threshold value in block 106, communications between the sensor module 24 and the smartphone 54 have been disrupted or are not at an acceptable level, so the method proceeds to block 108. In block 108, the recently collected data for the current period is stored in memory 28 on the sensor module 24. The stored data is associated with the current time period within the memory 28. Thus, when the data is recalled from memory 28, the time period when the data collected may also be retrieved.

If the determined signal strength is greater than the threshold value in block 106, communications between the sensor module 24 and the smartphone 54 are at an acceptable level, and the method proceeds to block 110. In block 110, the processor delivers the recently collected data to the transmitter 29, and the data is transmitted to the smartphone 54 for further processing.

After transmission of the data for the current time period in block 110, the method proceeds to block 112, where the processor 27 retrieves all the data stored in memory 28 for any previous time periods and delivers this data to the transmitter 29 for transmission to the smartphone 54. As mentioned above, the data transmitted from the memory 28 to the smartphone 54 includes time period information associated with the collected biometric data. Thus, when this data is received by the smartphone 54, the smartphone is provided with sufficient information to reconstruct the sequence of biometric data provided by the sensors 26 during the entire time communications with the sensor module 24 were disrupted. After transmission of this data from the memory 28, the processor clears the memory, wiping the memory clean of all data already transmitted to the smartphone 54.

Master/Slave Communications Arrangement

As described above, and as shown in FIG. 3, devices in an athletic performance monitoring network 18 include the sensor module 24, the watch 52, the smart phone 54, and devices connected to the smartphone 54 via the cloud 66. In at least one embodiment of the network 18, the senor module 24 communicates with the watch 52 and the smartphone 54 using Bluetooth® technology. This technology provides a peer-to-peer closed communication arrangement for wireless communications between the sensor module 24, the watch 52, and the smartphone 54. In this communication arrangement, a single device can only communicate with one other device at a given time (e.g., the sensor module 24 can only communicate with either the watch 52 or the smartphone 54, but cannot communicate with the watch 52 and the smartphone 54 at a given time). This limits the functionality of the devices during a sporting event. For example, if a user carries both the watch 52 and the smartphone 54 during an activity, only one of these devices serves as the output device, as the sensor module 24 is configured to communicate with only one other device at a given time.

Different scenarios are possible for use of the devices (i.e., the sensor module 24, the watch 52, and the smartphone 54) in the network 18. In a first scenario, a user participates in a sporting event using only the sensor module 24 and the phone 54. In a second scenario, the user participates in the sporting event using only the sensor module 24 and the watch 52. In a third scenario, the user participates in the sporting event using the sensor module 24, the watch 52 and the phone 54. In order for the third scenario to be used an embodiment of the network 18 may be utilized wherein the devices (e.g., 24, 52 or 54) communicate under a master/slave arrangement. In this master/slave arrangement, at least one of the devices is configured to selectively operate as either a master or a slave, depending on which devices are in communication with each other, as explained in further detail below.

Figure 5A:
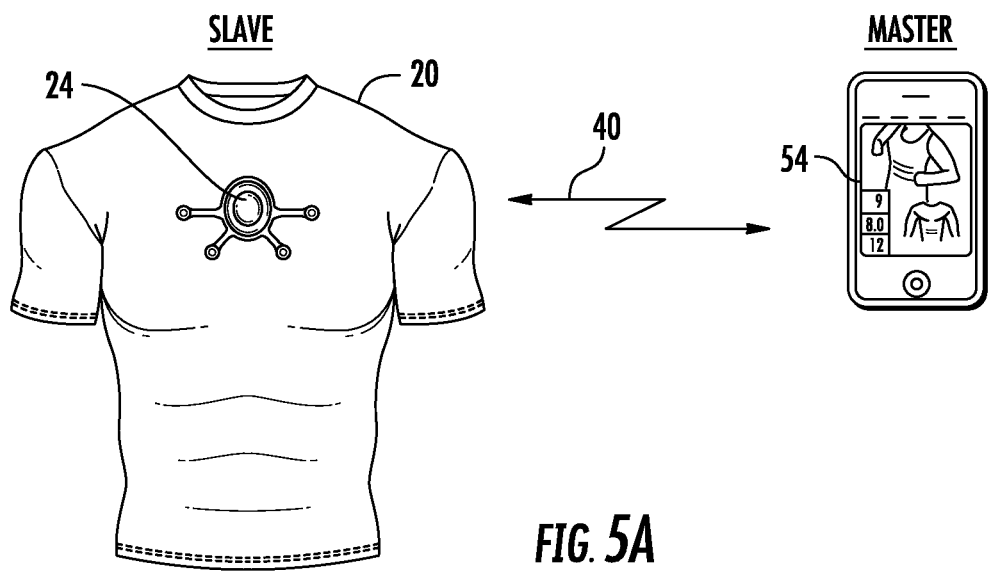
FIG. 5A is a diagrammatic view of a sensor module as a slave in communications with a smartphone as a master according to at least one alternative embodiment of the communications network of FIG. 3.

With reference now to FIG. 5A, in the first scenario under the master/slave arrangement, the sensor module 24 and the smartphone 54 are the two devices in communication during the sporting event. In this scenario, the smartphone 54 is the master and the sensor module 24 is the slave. Before communications are established between the sensor module 24 and the smartphone 54, the sensor module is in an advertising mode where it sends signals to alert any other devices in the area of its presence (i.e., "advertising"). However, in the advertising mode, the sensor module 24 does not transmit any biometric data or other collected sensor data. When the smartphone 54 receives the advertising signal from the sensor module, communications between the sensor module 24 and the smartphone 54 are established with the sensor module 24 acting as a slave and the smartphone 54 acting as a master. Accordingly, the sensor module 24 only transmits sensor data when instructed to do so by smartphone 54. Furthermore, once communications are established between the sensor module 24 and the smartphone 54, the sensor module 24 cannot communicate with any other devices, as its communications are locked to its master (the smartphone 54).

Figure 5B:
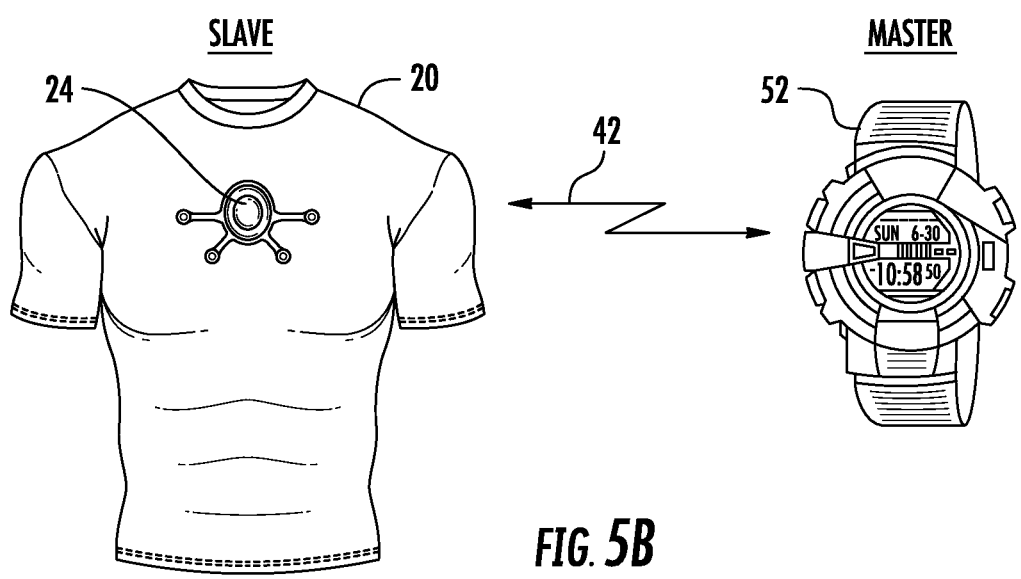
FIG. 5B is a diagrammatic view of a sensor module as a slave in communications with a watch as a master according to at least one alternative embodiment of the communications network of FIG. 3.

With reference now to FIG. 5B, in the second scenario under the master/slave arrangement, the sensor module 24 and the watch 52 are the two devices in communication during the sporting event. In this scenario, the watch 52 is the master and the sensor module 24 is the slave. Similar to the above-described sensor module/smartphone arrangement, after communications are established between the watch 52 and the sensor module 24, the sensor module 24 only transmits sensor data when instructed to do so by watch 52. Furthermore, once communications are established between the sensor module 24 and the watch 52, the sensor module 24 cannot communicate with any other devices, as its communications are locked to its master (the watch 52).

Figure 5C:
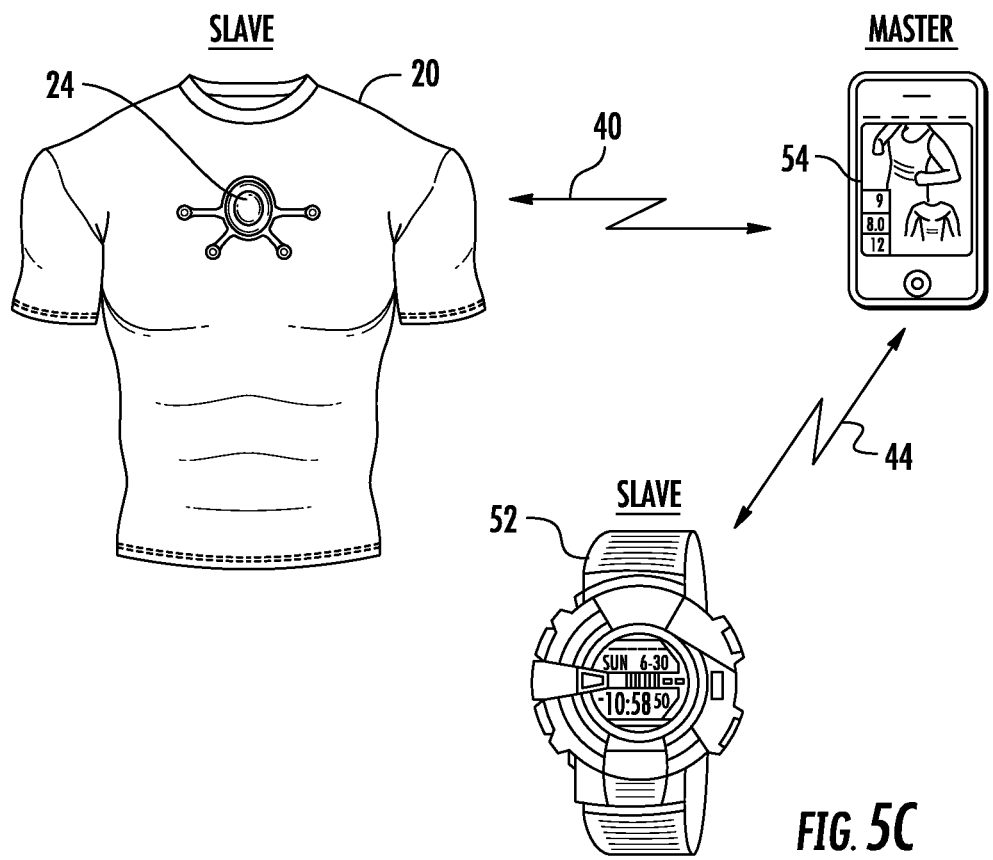
FIG. 5C is a diagrammatic view of a sensor module as a slave and a watch as a slave in communications with a smartphone as a master according to at least one alternative embodiment of the communications network of FIG. 3.

With reference now to FIG. 5C, in the third scenario under the master/slave arrangement, the sensor module 24, watch 52 and smartphone 54 are all in communication during a sporting event. In this scenario, the smartphone 54 is the master and the sensor module 24 and the watch 52 are both slaves. Similar to the above-described arrangements, after communications are established between the sensor module 24 and the smartphone 54, the sensor module 24 (a slave) only transmits sensor data when instructed to do so by smartphone 54 (the master). Additionally, after communications are established between the watch 52 and the smartphone 54, the watch 52 (a slave) only transmits sensor data when instructed to do so by smartphone 54 (the master). Once communications are established between the sensor module 24 and the smartphone 54, the sensor module 24 cannot communicate with any other devices, as its communications are locked to its master (the smartphone 54). Also, once communications are established between the watch 52 and the smartphone 54, the watch 52 is a slave and cannot communicate with any other devices, as its communications are locked to its master (the smartphone 54).

As explained above, in the third scenario the watch 52 acts as a slave in the communications arrangement, while in the second scenario the watch 52 acts as a master in the communications arrangement. Data from the sensor module 24 is still displayed on the watch 52 in the third scenario, but sensor data travels from the sensor module 24 to the smartphone 54 and from the smartphone 54 to the watch 52 in this situation, instead of data transfer directly from the sensor module 24 to the watch 52 as shown in FIG. 5B. However, this data transfer route of FIG. 5C is completely transparent to the user, and will appear to be no different than the scenario shown in FIG. 5B, as the user has no concern for the path the sensor data takes in travelling from the sensor module 24 to the watch 52.

The foregoing scenarios provide the user with great flexibility to use any of various devices during a workout. In particular, a user may choose to participate in a sporting event with or without the smartphone 54 and with our without the watch 52. Significantly, both the watch 52 and the smartphone 54 may be used to display or otherwise deliver data to the user during the sporting event should the user choose to use both the watch 52 and the smartphone. Thus, the user is not limited to the use of a single display device or a single data output device.

Figure 5D:
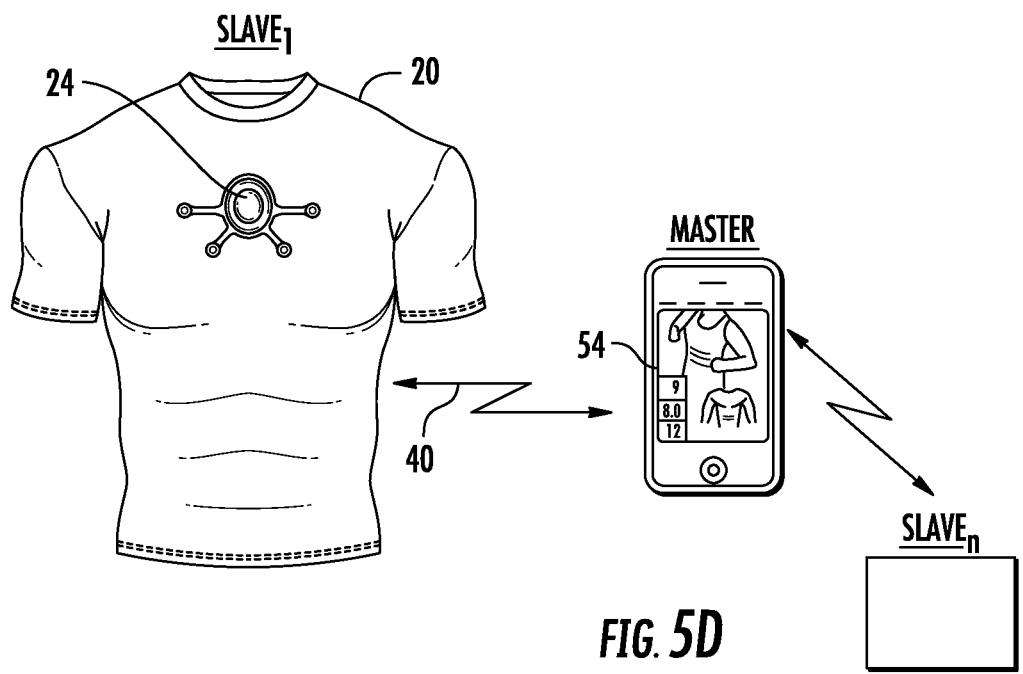
FIG. 5D is a diagrammatic view of a sensor module as a slave and an additional device as a slave in communications with a smartphone as a master according to at least one alternative embodiment of the communications network of FIG. 3.

The foregoing scenarios also illustrate the adaptability of the master/slave arrangement. In particular, the above-described master/slave arrangement is configured to allow additional devices to be added to the communications network. FIG. 5D illustrates this adaptability, showing that the smartphone 54 can be a master to as many slaves as are authenticated within the communications network. In particular, in FIG. 5D, the communications module 24 is a first slave and another device is the $n^{th}$ slave to the master smartphone 54. Accordingly, the above described communications network with the master/slave arrangement facilitates the addition of additional sensor devices as determined by the manufacturer, such as footwear sensors, headgear sensor, or any of various other sensors.

Figure 6:
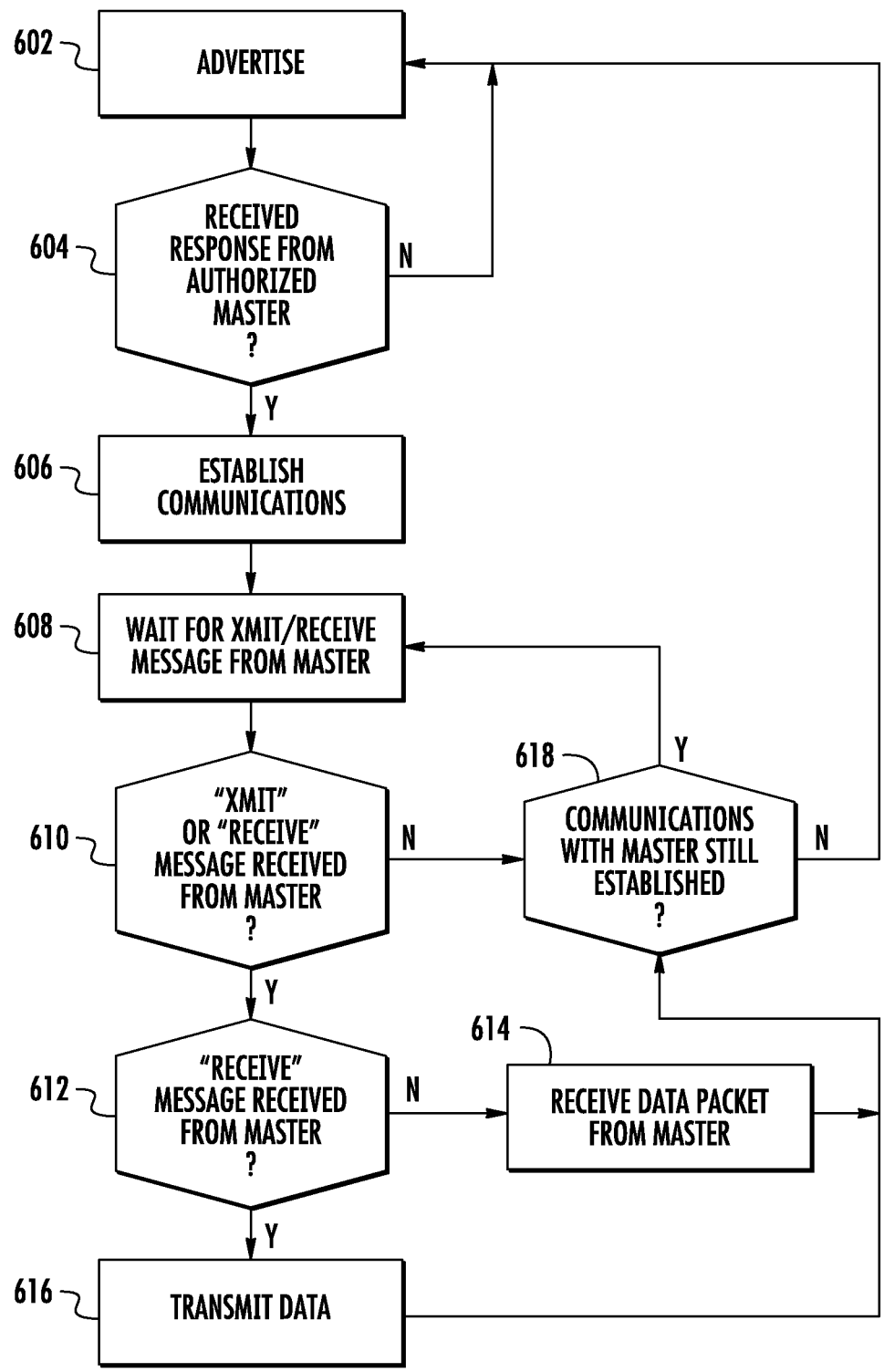
FIG. 6 is a flowchart of communications processing by a slave of the at least one alternative embodiment of the communications network of FIGS. 5A-5D.
Figure 7:
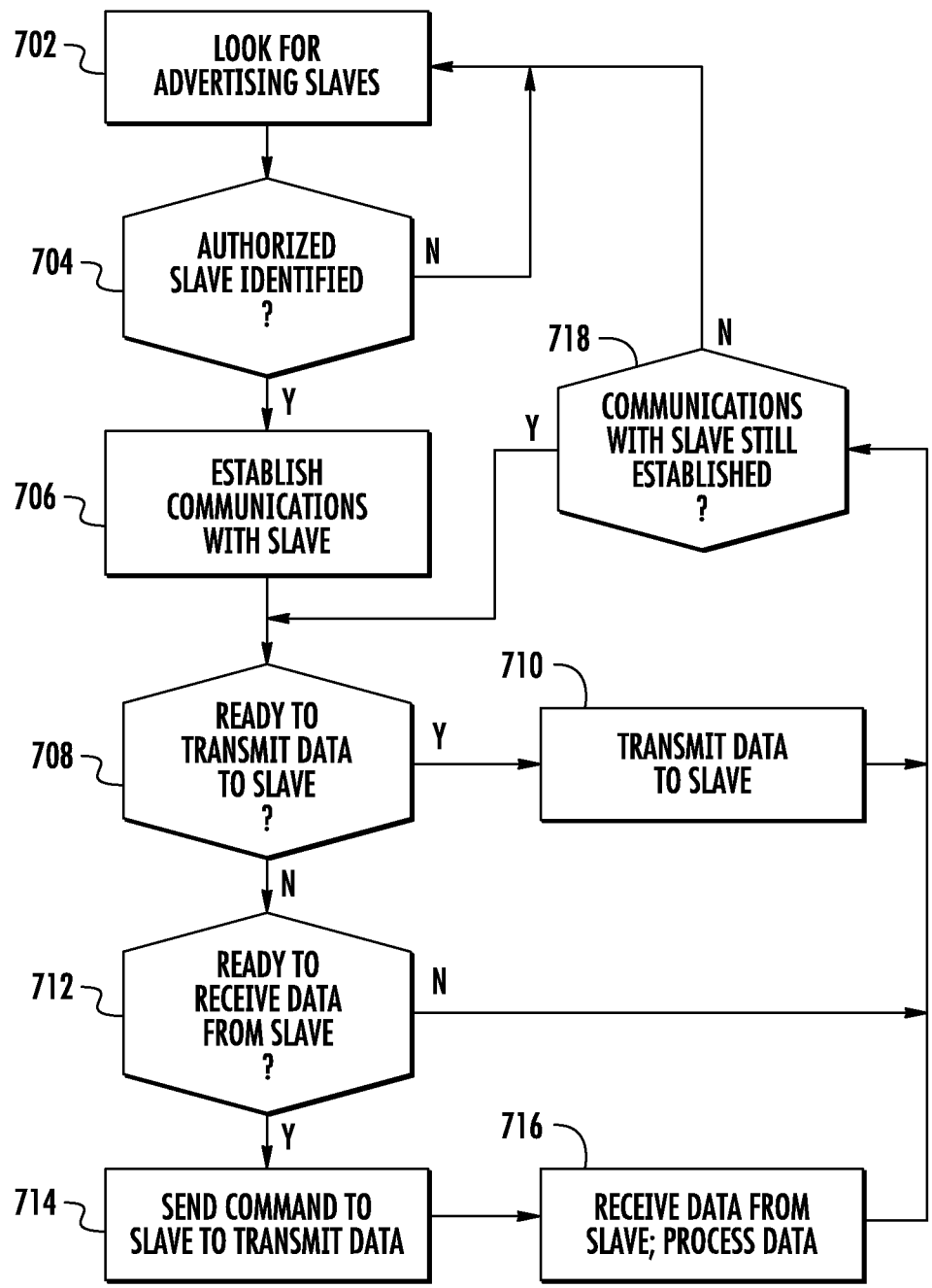
FIG. 7 is a flowchart of communications processing by a master of the at least one alternative embodiment of the communications network of FIGS. 5A-5D.
Figure 8:
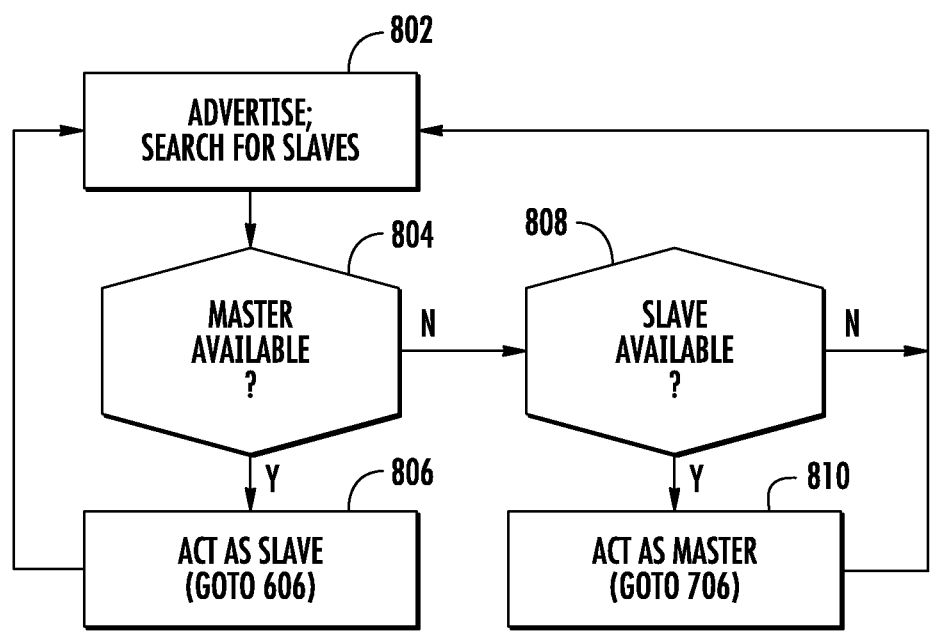
FIG. 8 is a flowchart of communications processing by a dual role device of the at least one alternative embodiment of the communications network of FIGS. 5A-5D.

The flowcharts of FIGS. 6-8 further illustrate communications activities of the various devices in the network in the above-described scenarios. FIG. 6 shows operation of the slaves (i.e., sensor module 24 or other slaves) when connecting to and communicating with a master. In step 602 of FIG. 6, the slave is in the advertising mode and sends out an advertising signal letting any masters (e.g., the smartphone 54 or the watch 52) in the transmission range know that the slave is available for data communications. In step 604, the slave determines whether a response to the advertise signal has been received from an authorized master. If a response from an authorized master has been received, the slave establishes communications with the master in step 606. Once communications between the slave and the master are established, the slave waits for a "transmit" or "receive" message from the master in step 608. As illustrated by this step, slave communications are dependent upon communications from the master at this point. In step 610, following the wait period of step 608, the slave determines whether a "transmit" or "receive" signal was received from the master. If no "transmit" or "receive" signal was sent, the slave determines whether communications with the master are still established in step 618. On the other hand, if a "transmit" or "receive" signal was sent, the slave processing continues in step 612 to determine whether the signal was a "receive" signal. If the signal from the master was a "receive" signal, the slave continues processing in step 614 and receives the data packet from the master. On the other hand, if the signal from the master was a "send" signal, the slave continues processing in step 616 and transmits the requested data to the master. Then, in step 618, the slave again determines if communications with the master are still established. If communications are established, the slave continues to wait for further instruction from the master in step 608. However, if communications with the master have been lost for some reason, the slave returns to the advertising mode, as shown in step 602.

FIG. 7 shows operation of the master (i.e., the smartphone 54 or other master) when connecting to and communicating with a slave. In step 702 of FIG. 7, the master is in a search mode looking for signals advertising slaves. In step 704, the master determines whether any of the signals received from advertising slaves are authorized slaves. If an authorized slave is identified, the master established communications with the authorized slave in step 706. Next, in step 708, the master determines whether the master is ready to transmit data to the slave. If the master is ready to transmit data to the slave, the master continues processing in step 710 and transmits one or more data packets to the slave. Alternatively, if the master is not prepared to transmit data in step 708, the master continues processing in step 712 and determines whether the master is ready to receive data from the slave. If the master is ready to receive data from the slave, the master sends a command to the slave in step 714, instructing the slave to transmit data. Then, in step 716, the master receives data from the slave and processes the data. This data processing may be internal within the master or may be sent elsewhere (e.g., the cloud 66) for further processing. Then, in step 718, the master determines whether communications with the slave are still established. If communications with the slave are still established, the master continues processing in step 708 and determines whether it is time to transmit data (or receive data in step 712). On the other hand, if communications with the slave have been disrupted, the master returns to the search mode in step 702 and continues looking for advertising slaves. In at least one alternative embodiment, step 718 is bypassed, and the master always returns to step 702 after either a data transmission or data reception. This allows the master to continually add new slaves to the communications network.

FIG. 8 shows operation of devices configured for selective operation as either a master or a slave (i.e., the watch 52 or other dual role devices). In step 802 of FIG. 8, the dual role device is in a search mode which includes both advertising as a possible slave and searching for slaves as a possible master. In step 804, the device determines whether an authorized master is available. If the master is available, the device begins to act as a slave in step 806. In particular, the device begins processing according to steps 606 to 618. In these steps, the device acts as a slave and takes instructions from the master before transmitting or receiving data. Once communications are disrupted with the master, the device returns to step 802 (instead of step 602). Alternatively, if no master is available in step 806, the device determines in step 808 whether an authorized slave is available for which the device can act as a master. If an authorized slave is available, the device continues processing according to steps 706 to 718. In these steps, the device acts as a master and instructs the slave when to transmit and receive data. Once communications are disrupted with the slave, the device returns to step 802 (instead of step 702).

Dynamic Proximity Pairing with Fixed Display Device

Figure 2B:
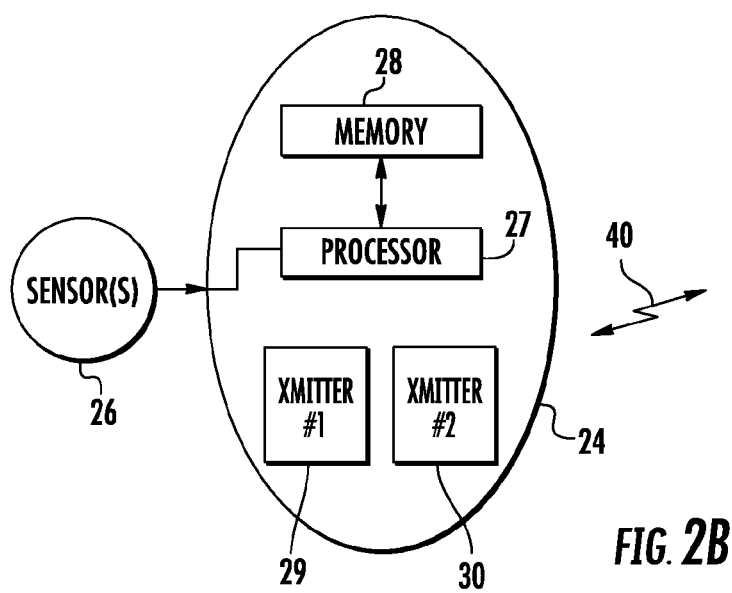
FIG. 2B is a is a block diagram of an alternative embodiment of the electronic components arrangement for the sensor module of FIG. 2A and a smartphone in communications with the sensor module.

In at least one embodiment of the network 18 the sensor module 24 is in communication with other devices based on dynamic proximity pairing. With reference to FIG. 2B, in this embodiment, the sensor module may be equipped with a second transmitter 30 (which may alternatively be simply a second transceiver) in addition to the first transceiver 29. While the first transceiver 29 communicates according to a first communications standard (e.g., Bluetooth as described above), the second transmitter 30 operates under a second communications standard (e.g., BlueRobin™, which provides for very low power consumption and a relatively long range). The second transmitter 30 provides for various additional functionality for the sensor module 24, and particularly features with respect to dynamic proximity pairing, as explained in further detail below.

Figure 9:
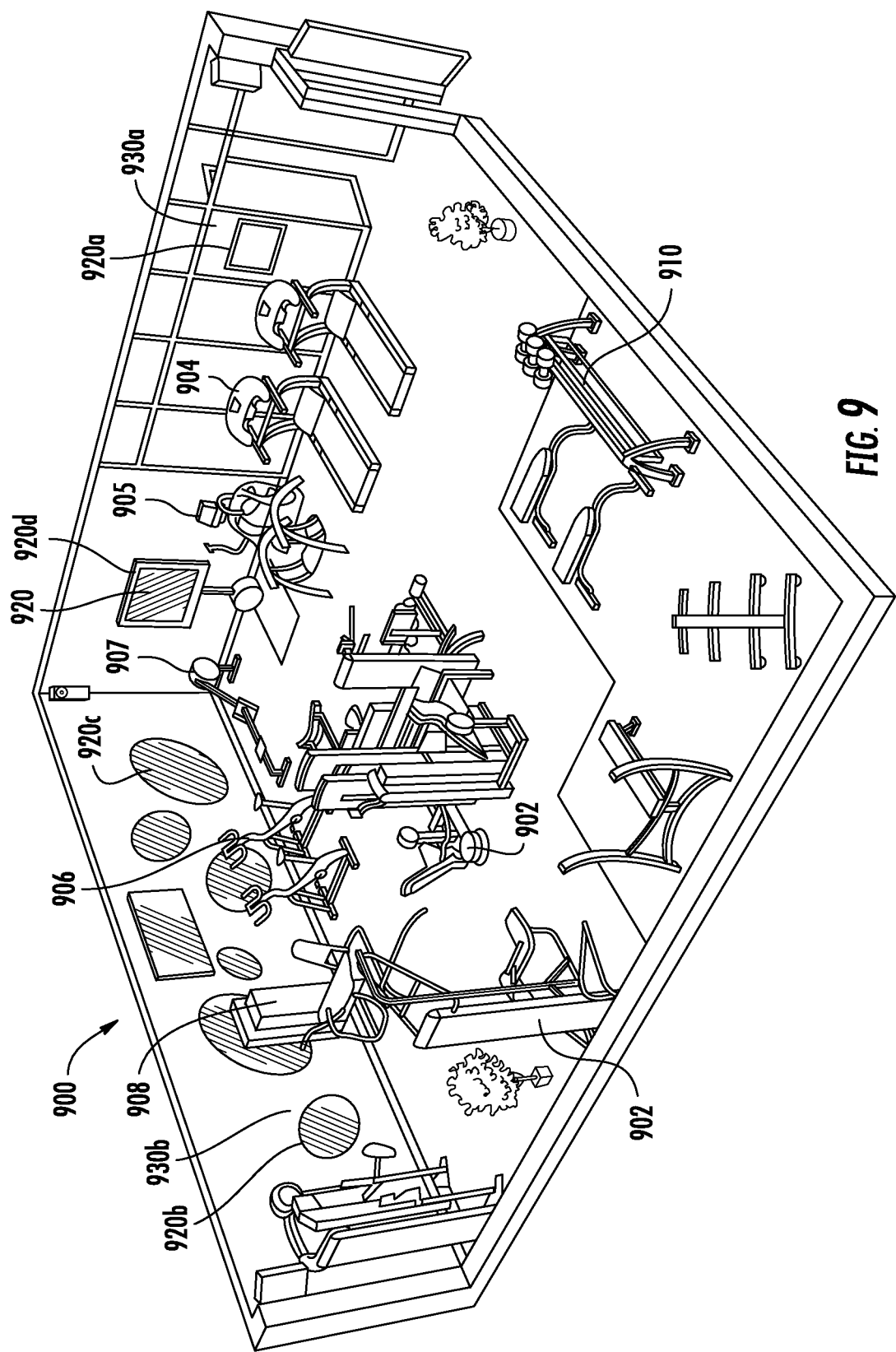
FIG. 9 is a perspective view of a gym including a plurality of fixed display devices configured to display data collected from the sensor module of FIG. 1.

An example of a network with dynamic proximity pairing is shown in FIG. 9. In FIG. 9, a gym 900 includes various workout stations 902 and associated exercise machines such as treadmills 904, elliptical machines 905, stationary bikes 906, rowing machines 907 and weight machines 908. The gym may also include one or more free weight stations 910 which may include benches and free weights that provide additional workout stations. Fixed display devices 920 are positioned in proximity of the various workout stations. A plurality of fixed display devices 920 are positioned throughout the gym 900. The fixed display devices 920 are configured to display data received from the second transmitter 30 of one or more sensor modules 24, provided a sensor module 24 is within a predetermined proximity of the fixed display device 920.

The fixed display devices 920 may be provided in any of various forms such as computer monitor screens, television screens, including LED and plasma screens, or electronic mirror displays/smart mirrors. One exemplary fixed display device is the smart mirror sold by Cybertexture (Mirror) Ltd. Smart mirrors are equipped with a reflective surface as well as various electronic components including a microprocessor. Accordingly, a smart mirror allows the user to see his or her reflection in combination with additional data that is electronically displayed on the mirror. The term "fixed display device" as used herein refers to a smart mirror or other display device that is mounted on a relatively stationary member, such as a vertical wall, floor, ceiling, kiosk, exercise machine, or other stationary member. A fixed display device is generally a device that is not portable by virtue of its mounting to a stationary member. However, a fixed display device may be mounted to the stationary member such that it is moveable or non-moveable relative to the stationary member. For example, a fixed display device may be pivotably or slideably mounted to a wall. Alternatively, the fixed display device may be fixedly mounted to the wall such that it is non-moveable relative to the wall. The term "wall" as used herein may refer to any of various human barriers, including ceilings, vertical walls, floors, glass walls, plaster walls, windows, doors, etc. A fixed display device that is mounted to a wall may be referred to herein as a "wall display device".

With reference again to FIG. 9, a plurality of fixed display devices 920 are positioned throughout the gym 900. For example, a first fixed display device 920a is mounted on a wall 930 in front of the treadmills 904. Because individuals on treadmills often watch television, the fixed display device 920a may be a television with an LCD screen. A second fixed display device 920b is mounted on a wall 930b in a location that is not associated with any workout station. This second fixed display device 920b is configured as a smart mirror that allows the user to check his or her appearance while at the same time viewing data related to one or more biometric parameters transmitted by the sensor device carried by the user. Other fixed display devices, such as fixed display devices 920c and 920d are positioned at other locations throughout the gym 900.

Figure 10:
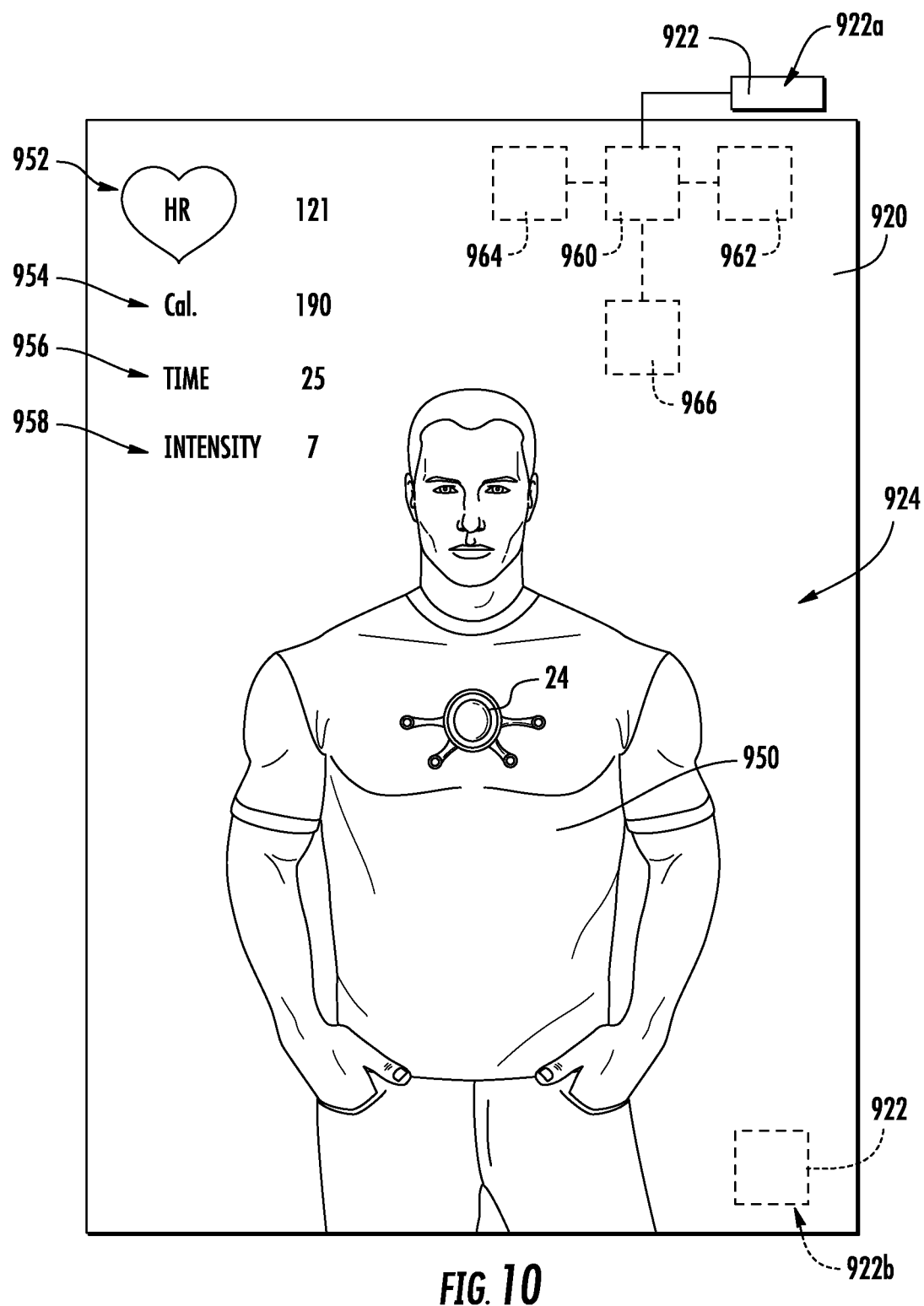
FIG. 10 is a front view of one of the fixed display devices of FIG. 9.

With reference now to FIG. 10, each of the fixed display devices 920 are configured to display real-time biometric data, performance data or other data for an individual carrying a sensor module 24 when the individual moves within a predetermined proximity of the fixed display device 920. To this end, each fixed display device 920 is configured with a proximity sensor 922 configured to detect the presence of a person within a predetermined range of the fixed display device 920. In the embodiment of FIG. 10, the fixed display device 920 is a smart mirror the reflection of an individual user 950 is shown on the reflective surface 924. The proximity sensor 922 may be positioned at any of various locations in or on the fixed display device 920, such as position 922a in FIG. 10 which is above or beside the reflective surface 924, or position 922b which is behind the reflective surface 924.

In addition to a proximity sensor 922, the fixed display device 920 further includes a processor 960, a memory 962, a transceiver 964, and display module 966. In FIG. 10, the processor 960, memory 962, transceiver 964 (which may alternatively be a simple receiver), and display module 966 are shown in dotted lines because they are positioned behind the reflective surface 924 and not apparent to the user. The proximity sensor 922 is connected to the processor 960 and delivers information concerning a detected user within the predetermined range to the processor 960. The processor 960 is connected to and controls data flow between the memory 962, the transceiver 964, and the display module. The memory 962 may include volatile and non-volatile memory and may store operating instructions and data for use in association with the fixed display device 920. For example, the memory 962 may store user profiles or sensor module data for various users registered to use the fixed display device 920. The transceiver 964 is configured to communicate with the transceiver of the sensor module 24 or handheld computing device 50 held by the user. The transceiver 964 is particularly configured to receive biometric data or other data transmitted from the sensor module 24 and pass it on to the processor 960 for display on the fixed display device 920. The display module 966 controls the reflective surface 924 such that at least a portion of the reflective surface 924 may be used to display data received from the processor 960.

The data displayed on the reflective surface 924 is biometric data or other data transmitted from the sensor module 24 worn by the user. For example, as shown in FIG. 10, current heart rate information for the user may be shown at position 952, calorie burn information for the workout period may be shown at position 954, total workout time may be shown at position 956, and workout intensity may be shown at position 958. It will be recognized by those of ordinary skill in the art that numerous other or different parameters may be shown on the fixed display device 920, such as average heart rate, current breathing rate, average breathing rate, anaerobic threshold, or any of various other biometric parameters or other data parameters that may be measured by a sensor and transmitted by the sensor module 24.

In addition to the display of biometric parameters, the fixed display device 920 may be configured to display other sensor data, information or messages which may be customized to particular users. For example, the fixed display device 920 may provide an encouraging message such as: "Nice Job!" or "Almost Finished!". As another example, the fixed display device 920 may provide a warning message such as: "Slow Down" or "Over 80% of Maximum Heart Rate". Furthermore, the fixed display device 920 may be connected to the internet and configured to provide general information that is consistent with a user profile that is stored in the fixed display device 920 and associated with the senor module 24 or transmitted to the fixed display device 920 when the user comes within proximity of the fixed display device 920. Examples of such general information includes current news or sports headlines, real-time scores or stock quotes, weather conditions or forecasts, or any of various other individualized data that may be of interest to the user. This individualized data may be determined by a personal profile associated with the sensor module and either stored within the fixed display device 920 or transmitted to the fixed display device when the user moves within the predetermined range of the fixed display device 920. When the user moves out of range of the proximity sensor of the fixed display device 920, the biometric data, personal messages, and individualized data are all removed from the fixed display device.

The proximity sensor 922 on the may take any of several forms, as will be recognized by those of ordinary skill in the art. In at least one embodiment, the proximity sensor may be an infrared sensor configured to detect infrared heat emitted from a human body. In another embodiment, the proximity sensor may simply be an rf receiver configured to receive an rf transmission from the low power transceiver associated with the sensor device 24. For example, the rf receiver may be a wireless receiver configured to receive rf communications transmitted with BlueRobin™ technology. Receipt of an rf transmission from another device (e.g., the transmitter 30 shown in FIG. 2A) will allow the rf receiver to determine that the rf transmitting device is within the predetermined range (e.g., based on RSSI). In addition to the foregoing, the proximity sensor may take any of various other forms as will be recognized by those of ordinary skill in the art, such as a capacitive photoelectric sensor configured to detect the shell 25 of the sensor module 24 (see FIG. 1) or other plastic target worn by the individual. In yet another embodiment, the proximity sensor may be an inductive proximity sensor configured to detect a special metal target worn by the individual. The special metal target may be a pin, badge or other metallic clip on device provided to all gym members or a select group of gym members.

The proximity sensor 922 detects when an individual, sensor module 24, or other defined target is within a predetermined range of the fixed display device 920. For example, in at least one embodiment, the proximity sensor 922 is used to determine that an individual is within a predetermined range of ten feet from the fixed display device 920. In yet another embodiment, the proximity sensor 922 is used to determine that an individual is within a predetermined range of five or six feet of the fixed display device. This predetermined range may be advantageous for fixed display devices 920 used in association with treadmills 904, elliptical machines 905, or stationary bikes 906. In yet another embodiment, the proximity sensor 922 is used to determine that an individual is within a predetermined range of two or three feet of the fixed display device. This predetermined range may be advantageous for fixed display devices 920 used in association with fixed display devices 920 that are not associated with a specific workout station 902. Various proximity sensors may be calibrated to set a specific predetermined range of detection for the proximity sensor. For example, an infrared proximity sensor may be adjusted to detect infrared light at various ranges from 2 feet to 20 feet or more from the proximity sensor 922.

In at least some embodiments, the fixed display device 920 is configured to display biometric data and individualized data for only a single user 950. In these embodiments, the first sensor module 24 to be detected by the fixed display device 920 is the sensor module 24 for which the fixed display device 920 displays information. In other embodiments, the fixed display device 920 may be configured to display biometric and individualized data for multiple users, such as two, three or four users. However, even in these embodiments configured to display data for multiple users, the fixed display device has a maximum number of users for which data can be displayed, and additional users are blocked out until a current user moves out of range from the display device. In embodiments configured to display data for multiple users, the proximity sensor 922 may be configured to distinguish the position of the multiple users relative to the reflective surface 924 (or other display surface) and display the received biometric data for each user in the associated position on the reflective surface. For example, FIG. 13 shows a top view of a fixed display device 920 with two users 1310 and 1320 positioned in front of the fixed display device. In this scenario, one or more proximity sensors are used to detect targets in a plurality of ranges associated with the fixed display device, including ranges 1330a, 1330b, and 1330c. User 1310 is mostly in range 1330a, and user 1320 is mostly in range 1330c in FIG. 13. Accordingly, sensed biometric data from user 1310 will be shown on the left side 1312 of the fixed display device 920, and biometric data from user 1320 will be shown on the right side 1322 of the fixed display device.

Figure 11:
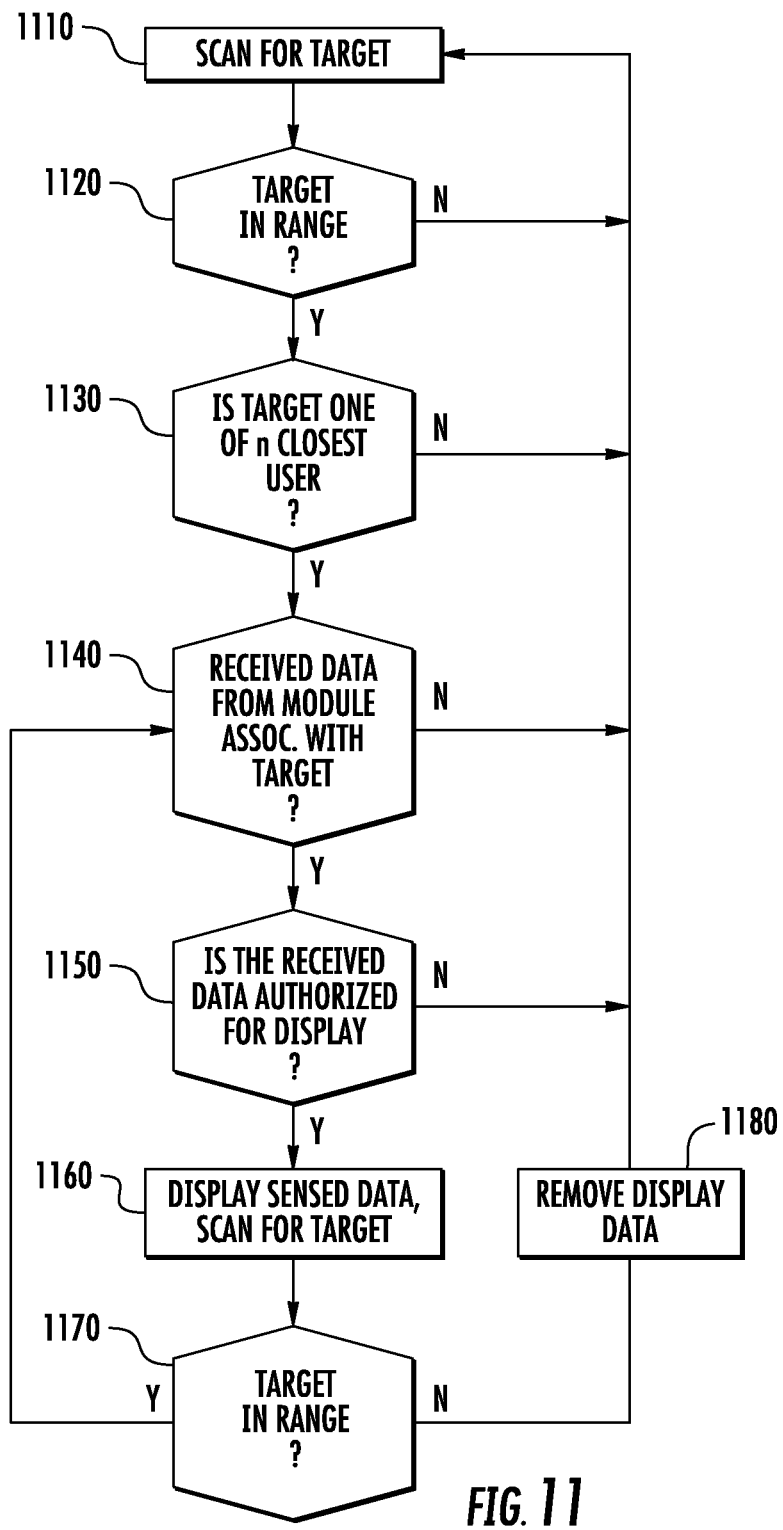
FIG. 11 is a flowchart of a first method of operating the fixed display device of FIG. 10.

With reference now to FIG. 11, a flowchart is shown illustrating a method of operating a fixed display device, such as a smart mirror, with dynamic proximity pairing. The method begins with block 1110 where the proximity sensor 922 of the fixed display device 920 scans for a target (e.g., an individual or sensor module 24) within a predetermined range of the fixed display device 920. If no targets are within range in block 1120, the method returns to block 1110 and the proximity sensor 922 continues to scan for targets within the predetermined range. However, if a target is within range in block 1120, the method continues to block 1130 where the fixed display device determines if the target is one of the n closest targets, where n is the maximum number of users that can be displayed on the fixed display device. Then, in block 1140, after identifying a target within range, a determination is made whether data has been received from a transmitter associated with the target. This transmitter may be, for example, the second transmitter 30 of the sensor module 24, as shown in FIG. 2B. If data has been received from a transmitter associated with the target, the fixed display device 920 associates the transmitter with a particular user profile in a database stored in memory 962. Next, in step 1150, the fixed display device checks the user profile to determine whether the user has indicated that the type of data received is an authorized parameter for display on the particular fixed display device (e.g., if the fixed display device 920 is a public display, only limited data may be displayed; if the fixed display device 920 is an authorized private display, more detailed data may be displayed). For example, a user may indicate that the user's heart rate is an authorized parameter for a public display (i.e., on a publicly viewable fixed display device) but that the user's intensity level, breathing rate, or other parameter is not an authorized parameter for public display. Accordingly, the user or administrator may manipulate his or her user profile in the system to determine what biometric or other data will be available for third parties to see when they move into range of a fixed display device, depending on the type of fixed display device. Alternatively, signals from the sensor module 24 may include a prefix that indicates whether the transmitted data is authorized for display by public network devices. In this embodiment, the user may pre-configure the sensor module to transmit authorized parameter information along with sensed biometric data.

If the received data is authorized for display on a particular fixed display device, the fixed display device 920 displays the received data at block 1160. The received data is displayed for some limited period of time, (e.g., two to ten seconds) and then the proximity sensor 922 again scans for a target within the predetermined range. At block 1170, a determination is made whether the target remains within the predetermined range. If a target remains within the predetermined range, the fixed display device returns to block 1140 and determines whether any new data is available for display (e.g., updated heart rate information). If no target remains within the predetermined range, the previously displayed data is removed from the display in block 1180. The method then returns to block 1210 and continues to scan for new targets that enter the predetermined range of the fixed display device 920.

In at least one embodiment where the sensor module 24 only includes one transceiver 29, the fixed display devices 920 may be configured to join a network 18 of devices, such as the network 18 described above, when an individual with a sensor module 24 comes within the predetermined range of the fixed display device 920. The network 18 to be joined includes the sensor module 24 and may further include additional devices such as a watch 52, a smartphone 54, or other network device, as described above with reference to FIG. 3. Upon joining the network 18, the fixed display device 920 is configured for selective operation as either a master or a slave. Accordingly, when an appropriate target (i.e., individual, sensor module shell 25, or other target depending on the type of proximity sensor) comes within the predetermined range of a fixed display device 920, the fixed display device 920 begins processing according to the flow chart of FIG. 8. By operating in this manner, the fixed display device determines whether it will act as a master or a slave within the network 18. As explained in further detail below, determination whether the fixed display device 920 will operate as a master or a slave in the wireless network depends on the presence of other devices in the network In step 802 of FIG. 8, the fixed display device 920 is in a search mode which includes both (i) advertising as a possible slave and (ii) searching for slaves as a possible master. In step 804, the device determines whether an authorized master is available. If a master is available (e.g., a smartphone 54, watch 52 or other network device configured to act as a master within the network 18), the fixed display device 920 begins to act as a slave. An example of such a network arrangement is shown in FIG. 11A with the sensor module 24 and smartphone 54 both within a predetermined range 560 of the proximity sensor 922 of the fixed display device 920. When the fixed display device 920 joins the network as a slave, the fixed display device 920 begins processing according to steps 606 to 618 shown in FIG. 6. As discussed previously, in these steps the fixed display device 920 acts as a slave and takes instructions from the master (i.e., smartphone 54) before receiving or displaying data. Communications with the master will generally continue as shown in FIG. 6 as long as the individual or sensor module 24 stays within the predetermined range of the proximity sensor 922. However, once the individual or sensor module 24 moves outside of the predetermined range of the proximity sensor, the fixed display device 920 ceases communications within the network 18, including any established communications with the master. Once communications are ceased, the fixed display device 920 takes no further action until the proximity sensor detects an individual or sensor module 24 within the predetermined range.

When the fixed display device 920 again detects an individual or sensor module 24 within the predetermined range, the fixed display device 920 returns to step 802 of FIG. 8. If no master is available in step 806, the fixed display device determines in step 808 whether an authorized slave (i.e., the sensor module 24) is available for which the fixed display device can act as a master. If an authorized slave is available, the fixed display device 920 begins to operate as a master. An example of such a network arrangement is shown in FIG. 11B with the sensor module 24 (but no smartphone) within a predetermined range 560 of the proximity sensor 922 of the fixed display device 920. When the fixed display device 920 joins the network 18 as a master, the fixed display device 920 begins processing according to steps 706 to 718 of FIG. 7, as discussed previously. In these steps, the fixed display device 920 acts as a master and instructs the sensor module 24 when to transmit and receive data. Once the individual or sensor module 24 moves outside of the predetermined range of the proximity sensor, the fixed display device 920 ceases communications within the sensor module 24 within the network 18. Once communications are ceased, the fixed display device 920 takes no further action until the proximity sensor detects an individual or sensor module 24 within the predetermined range.

Figure 12A:
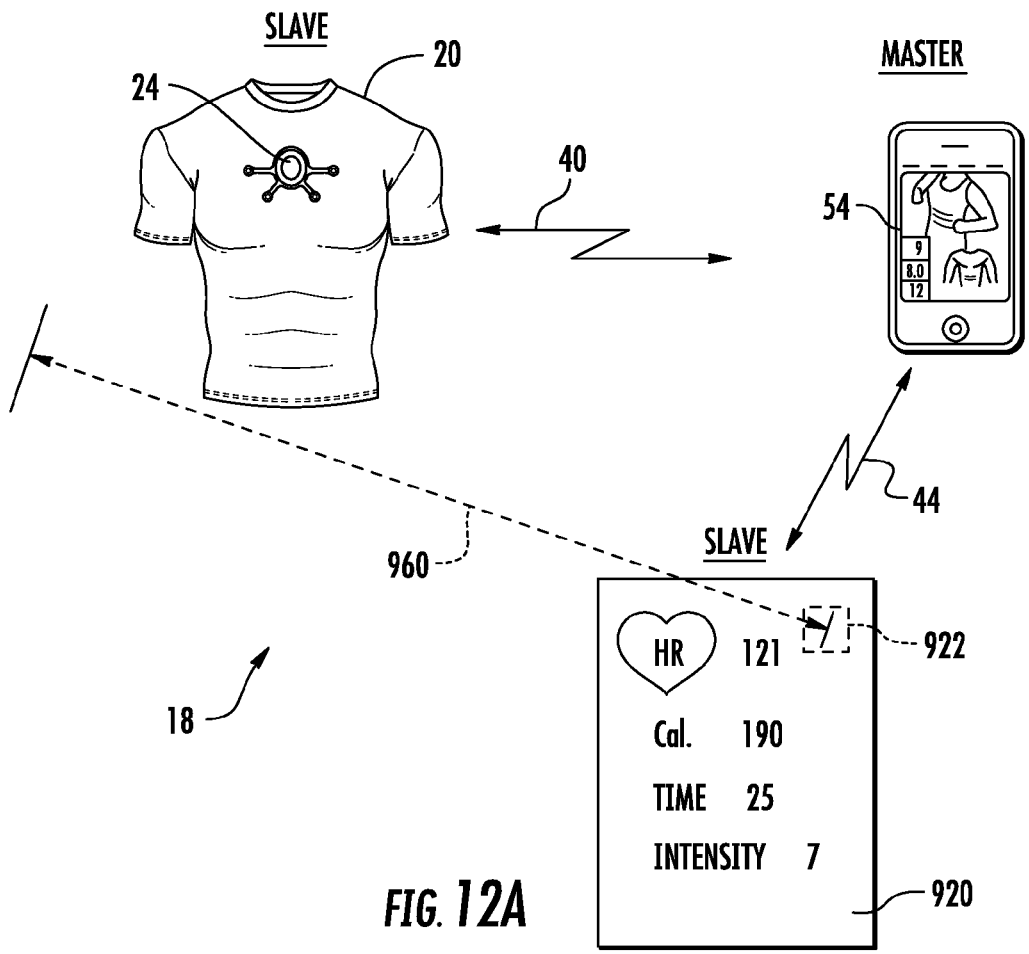
FIG. 12A is diagrammatic view of a sensor module as a slave and a smart mirror as a slave in communication with a smartphone as a master according to at least one alternative embodiment of the communications network of FIG. 3.
Figure 12B:
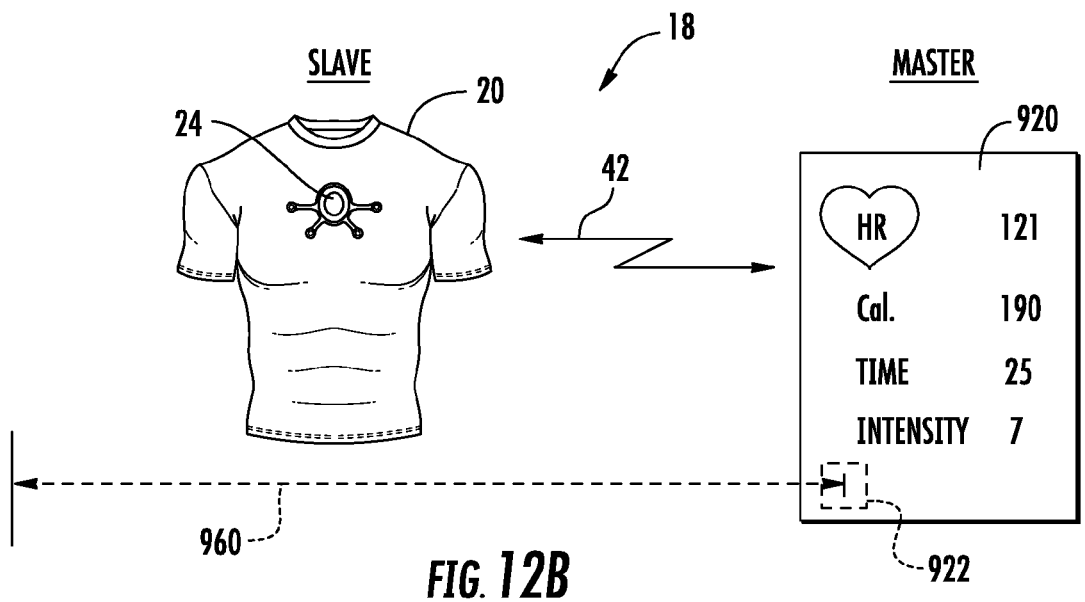
FIG. 12B is a diagrammatic view of a sensor module as a slave in communications with a smart mirror as a master according to at least one alternative embodiment of the communications network of FIG. 3.
Figure 12C:
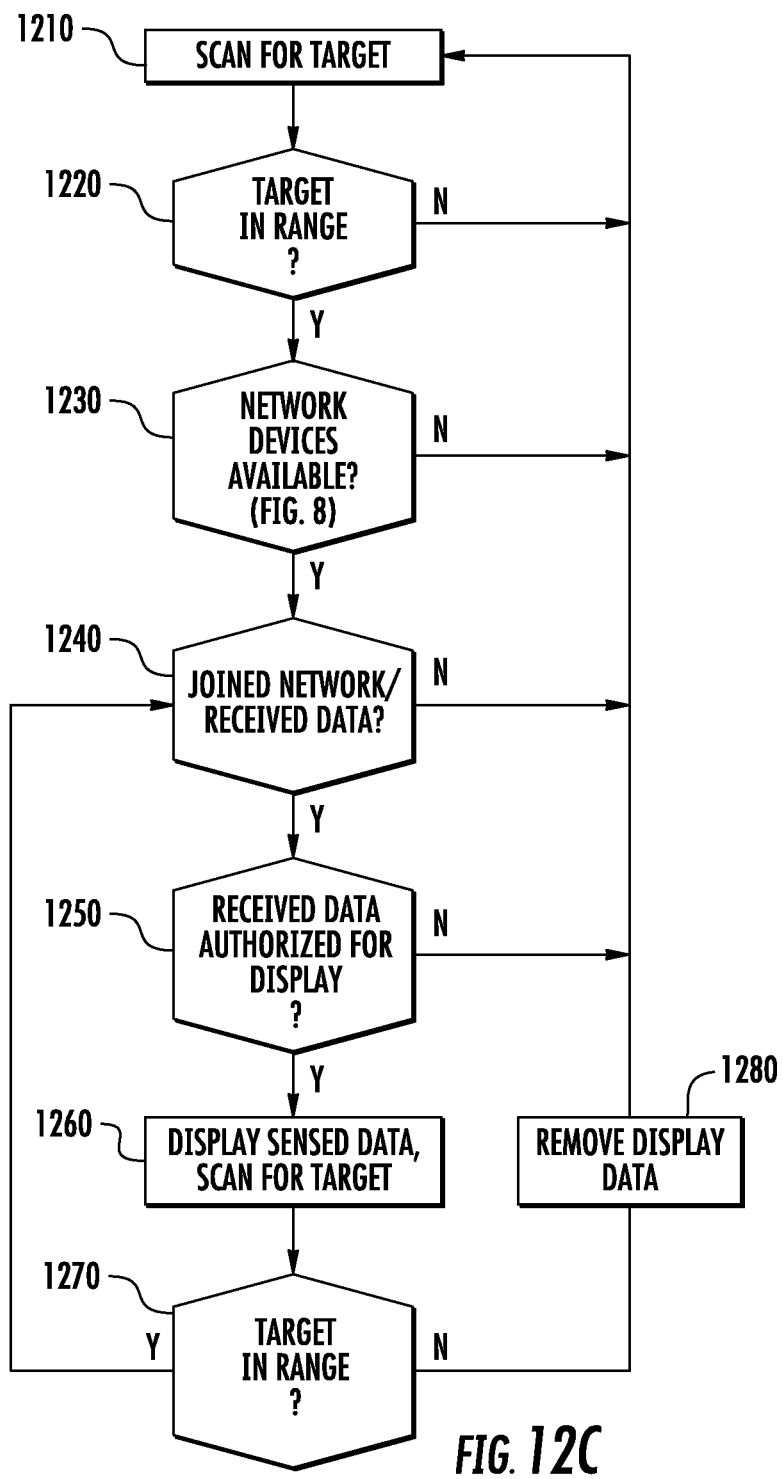
FIG. 12C is a flowchart of a second method of operating the fixed display device of FIG. 10.

With reference now to FIG. 12C, a flowchart is shown illustrating a method of operating a fixed display device, such as a smart mirror, in the above-described network arrangement. The method begins with block 1210 where the proximity sensor 922 of the fixed display device 920 scans for a target (e.g., an individual or sensor module 24) within a predetermined range of the fixed display device 920. If no targets are within range in block 1220, the method returns to block 1210 and the proximity sensor 922 continues to scan for targets within the predetermined range. However, if a target is within range in block 1220, the method continues to block 1230 where the fixed display device determines if network devices are available for communication by attempting to join the network as either a master or a slave device according to the process shown in FIG. 8, and described above. Then in block 1240, after attempting to join the network and establish communications as either a master or a slave device, the fixed display devices determines whether network communications have been established and data received from another network device. If data has been received from another network device, the fixed display device determines in block 1250 whether the received data is authorized for display. Accordingly, signals from the sensor modules 24 may include a prefix that provides an identification of the sensor module sending the signal. Once the fixed display device 920 has an identification of the sensor module sending the signal, the fixed display device may check a user profile in the memory to determine whether the user has indicated that the type of data received is an authorized parameter for display on public network devices (i.e., fixed display devices 920). For example, a user may indicate that the user's heart rate is an authorized parameter for display but that the user's intensity level, breathing rate, or other parameter is not an authorized parameter for display. Accordingly, the user may manipulate his or her user profile in the system to determine what biometric or other data will be available for third parties to see when they move into range of a fixed display device. Alternatively, signals from the sensor module 24 may include a prefix that indicates whether the transmitted data is authorized for display by public network devices. In this embodiment, the user may pre-configure the sensor module to transmit authorized parameter information along with sensed biometric data.

If the received data is authorized for display, the fixed display device 920 displays the received data at block 1260. The received data is displayed for some limited period of time, (e.g., two to ten seconds) and then the proximity sensor 922 again scans for a target within the predetermined range. At block 1270, a determination is made whether the target remains within the predetermined range. If a target remains within the predetermined range, the fixed display device returns to block 1240 and determines whether any new data is available for display (e.g., updated heart rate information). If no target remains within the predetermined range, the previously displayed data is removed from the display in block 1280. The method then returns to block 1210 and continues to scan for new targets that enter the predetermined range of the fixed display device 920.

Dynamic Proximity Pairing with Team Concept

In at least one embodiment, dynamic proximity pairing provides for a method of quickly and easily associating each of multiple communications modules with a member of a team or other group of athletes during a training session or other athletic event. In this embodiment, each sensor module 24 is equipped with two different transmitters as shown in FIG. 2B. The first transmitter 29 is a transceiver and is configured to communicate within a network with other network devices, such as smartphone 54 or watch 52, according to a first communications protocol, such as a protocol under the Bluetooth® communications technology. The second transmitter is configured to transmit data under a second communications protocol that is different from the first communications protocol. For example, the second communications protocol, such as a protocol provided under the BlueRobin™ communications technology.

FIG. 14 shows an exemplary dynamic proximity pairing arrangement 140 for use during a group training session or athletic event. The arrangement 140 includes a plurality of sensor modules 24a-24n to be used by a plurality of individual team members 150*a*-150*n*. A computing device 160 (e.g., a desktop computer or a handheld computing device) is configured to receive data from the sensor modules 24*a*-24*n* via a transceiver 170 connected to or provided within the computing device 160. The transceiver 170 is configured for communications using the communications protocol of the first transmitter 29 in the sensor modules 24*a*-24*n* (e.g., a protocol provided under the BlueTooth® communications technology). While the transceiver 170 is shown in FIG. 15 as being separate from the computing device 160 and attached thereto by a cable, it will be recognized that the transceiver 170 may also be included within the computing device 160.

A registration device 180 is also connected to the computing device 160. The registration device 180 provides a registration surface 182 on which a sensor module 24 may rest or be positioned in close proximity therewith. When a sensor module 24 is positioned in positioned in close proximity to the registration surface 182, an identification number for the sensor module is delivered to the computing device 160, as explained in further detail below. The registration device 180 is generally a small box or other housing that contains a transceiver, a memory and a processor or other electronic devices. The registration device 180 is configured to communicate with the second transmitter 30 in the sensor modules 24*a*-24*n* (e.g., a protocol provided under the BlueRobin™ communications technology). The registration device 180 is used to associate each of the sensor modules 24*a*-24*n* with each of the individual team members 150*a*-150*n*. While the registration device 180 is shown in FIG. 14 as being separate from the computing device 160 and connected thereto with a cable, it will be recognized that the registration device 180 may also be included as part of the computing device 160.

When a team member 150*a*-150*n* wears or otherwise carries one of the sensor modules 24*a*-24*n*, data collected for the team member 150*a*-150*n* is transmitted to the computing device 160 via the first transmitter 29 within the sensor module. Transmission of this data may be according to any of various protocols and may be established based on the master/slave communications arrangement described previously. However, for the transmitted data to be associated with a particular team member, the sensor module transmitting the data must also be associated with the team member. If the team member is carrying one of the sensor modules 24*a*-24*n*, but the sensor module has not been associated with the team member within the computing device 160, there will be no way of knowing that the transmitted data should be associated with the team member from which the data was collected. To this end, each of the sensor modules 24*a*-24*n* includes a unique identification number 190 (e.g., a serial number) that identifies that particular sensor module. This unique identification number 190 is contained within the memory of the sensor module 24 and is also printed on the housing of the sensor module (e.g., a visible number or barcode printed on a tag or etched in the housing). In order to associate each team member with a particular sensor module 24*a*-24*n*, the identification number must be associated with the team member 150*a*-150*n* wearing the sensor module.

One method for associating a team member 150*a*-150*n* with a sensor module 24*a*-24*n* is the manual process of a human registrar or other individual reading the identification number, typing the identification number into the computing device 160, and associating the identification number with the name of the player in an application on the computing device 160 at the time the sensor module is given to the team member. However, this process is cumbersome and time consuming, as the identification numbers on the sensor modules are often small and difficult to read. Moreover, errors may occur as the human registrar 196 types the identification number into the computing device 160.

In view of the above, an alternative method is provided for associating each of the sensor modules 24*a*-24*n* with each of the team members 150*a*-150*n*. According to this advantageous method, the second transmitter 30 within the sensor module 24 transmits the identification number for the sensor module and provides the opportunity for more conveniently associating each sensor module 24*a*-24*n* with one of the team members 150*a*-150*n*. In particular, as shown by arrow 192 in FIG. 14, prior to distributing a selected sensor module (e.g., 24*c*) to one of the team members (e.g., 150*c*), the registrar 196 brings the selected the sensor module 24*c* into proximity of the registration surface 182 of the registration device 180. Based on the proximity of the sensor module 24*c* to the registration device 180 (e.g., using RSSI technology or other proximity sensing technology), the registration device 180 reads the identification number 190 that is periodically transmitted by the second transmitter 30 of the sensor module 24*c* and delivers the identification number 190 to the computing device 160. Then, the application running on the computing device 160 automatically associates a team member 150*c* with the sensor module 24. That sensor module 24*c* is then distributed to the team member 150*c* by the registrar 196, as shown by arrow 194 of FIG. 14.

In the embodiment of FIG. 15, a list of team members is shown on a display screen. When a sensor module 24*a*-24*c* is brought into proximity with the registration device 180, the computing device automatically associates the identification number 190 for that sensor module with the next team member on the list. For example, in FIG. 15, the sensor module with identification number A5678C was previously associated with Joe Flacco and the identification number A1234B was previously associated with Peyton Manning. The identification number for the next sensor module brought into proximity of the registration device 180 will be assigned to Andrew Luck, who is listed as the next team member in the list. In another alternative embodiment, each identification number appearing on the screen is not assigned to a subsequent team member on the list, but instead, the registrar selects (e.g., with a screen tap or a mouse click) a name on the list of team members in order to assign the identification number to that team member. The dynamic proximity pairing of identification numbers for sensor modules to team members not only makes it easy to initially pair an identification number with a particular team member, but also makes it easy to quickly and easily switch identification numbers from one player to the next. For example, if only a limited number of sensor modules 24 are available and multiple teams are interested in using the sensor modules, the sensor modules may be used for a first team for a first period of time after which they are returned to the registrar and then reassigned to the players of a second team.

Although the physiological data management system and method has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of any appended claims should not be limited to the description of the preferred embodiments contained herein.

What is claimed is:

1. A method of monitoring biometric data for an individual comprising:
   sensing a biometric parameter of the individual with a sensor carried by the individual;
   receiving the at least one biometric parameter at a transceiver carried by the individual, the transceiver in a wireless communication network with a handheld computing device and a receiver associated with a fixed display device, wherein the fixed display device is a wall display;
   transmitting the sensed biometric parameter from the transceiver to the handheld computing device;
   detecting that the individual has moved within a predetermined range of the fixed display device;
   wirelessly transmitting the sensed biometric parameter from the handheld computing device to the receiver associated with the fixed display device after the detection that the individual has moved within the predetermined range;
   displaying the sensed biometric parameter of the individual on the fixed display device;
   detecting that the individual has moved outside of the predetermined range; and
   removing the sensed biometric parameter of the individual from the fixed display device after detecting that the individual has moved outside of the predetermined range.

2. The method of claim 1 wherein the wall display is a smart mirror.

3. The method of claim 2 wherein the smart mirror is one of a plurality of fixed display devices mounted in a gym.

4. The method of claim 1 wherein detecting that the individual has moved within a predetermined range of the fixed display device comprises detecting that a target carried by the individual is within a predetermined range of the fixed display device.

5. The method of claim 1 wherein the biometric parameter is a heart rate or a breathing rate.

6. The method of claim 1 wherein the fixed display device is configured to operate as a master or a slave device in a wireless network depending on other devices present in the network.

7. The method of claim 1 further comprising determining that the sensed biometric parameter is an authorized parameter for display in a user profile before displaying the sensed biometric parameter of the individual on the fixed display device.

8. A method of monitoring biometric data for an individual comprising:
   sensing a biometric parameter of the individual with a sensor carried by the individual;
   receiving the at least one biometric parameter at a transceiver carried by the individual, the transceiver in a wireless communication network with a handheld computing device and a receiver associated with a fixed display device;
   transmitting the sensed biometric parameter from the transceiver to the handheld computing device;
   detecting that the individual has moved within a predetermined range of the fixed display device;
   wirelessly transmitting the sensed biometric parameter from the handheld computing device to the receiver associated with the fixed display device after the detection that the individual has moved within the predetermined range;
   determining that the sensed biometric parameter is an authorized parameter for display in a user profile;
   displaying the sensed biometric parameter of the individual on the fixed display device;
   detecting that the individual has moved outside of the predetermined range; and
   removing the sensed biometric parameter of the individual from the fixed display device after detecting that the individual has moved outside of the predetermined range.

9. The method of claim 8 wherein the user profile is stored in a memory in the fixed display device.

10. The method of claim 8 wherein the fixed display device is a smart mirror.

11. A system for monitoring biometric data for an individual, the system comprising:
    a sensor configured to sense a biometric parameter of an individual carrying the sensor;
    a transceiver configured to be carried by the individual, the transceiver further configured to receive the sensed biometric parameter from the sensor and transmit the sensed biometric parameter upon receiving instructions from another device in a wireless network arrangement;
    a handheld computing device in the wireless network arrangement with the transceiver, the handheld computing device configured to be carried by the individual, the handheld computing device further configured to receive the sensed biometric parameter transmitted by the transceiver and retransmit the sensed biometric parameter; and
    a fixed display device in the wireless network arrangement with the transceiver and the handheld computing device, the fixed display device being a wall display configured to (i) determine that a target is within a predetermined range of the fixed display device, (ii) receive the sensed biometric parameter transmitted by the handheld computing device, (iii) display the sensed biometric parameter on a display screen when the target is within the predetermined range, and (iv) remove the sensed biometric parameter from the display screen after the target is outside of the predetermined range.

12. The system of claim 11 wherein the wall display is a smart mirror.

13. The system of claim 12 wherein the target is a first target and the smart mirror is further configured to (i) determine that a second target is within the predetermined range of the fixed display device, (ii) receive a second wireless transmission including a second sensed biometric parameter associated with the second target, (iii) display the sensed biometric parameter associated with the second target on the display screen when the second target is within the predetermined range, and (iv) remove the sensed biometric parameter associated with the second target from the display screen after the second target is outside of the predetermined range.

14. The system of claim 11 wherein the fixed display device is configured to operate as a master or a slave device in the wireless network arrangement depending on other devices present in the network.

15. The system of claim 11 wherein the biometric parameter is a heart rate or a breathing rate.

16. The system of claim 11 wherein the target is a sensor module worn by the individual.

17. The system of claim 11 wherein the fixed display device is further configured to determine that the sensed biometric parameter is an authorized parameter for display in a user profile.

18. A system for monitoring biometric data for an individual, the system comprising:
- a sensor configured to sense a biometric parameter of an individual carrying the sensor;
- a transceiver configured to be carried by the individual, the transceiver further configured to receive the sensed biometric parameter from the sensor and transmit the sensed biometric parameter upon receiving instructions from another device in a wireless network arrangement;
- a handheld computing device in the wireless network arrangement with the transceiver, the handheld computing device configured to be carried by the individual, the handheld computing device further configured to receive the sensed biometric parameter transmitted by the transceiver and retransmit the sensed biometric parameter; and
- a fixed display device in the wireless network arrangement with the transceiver and the handheld computing device, the fixed display device being a wall display configured to (i) determine that a target is within a predetermined range of the fixed display device, (ii) receive the sensed biometric parameter transmitted by the handheld computing device, (iii) determine that the sensed biometric parameter is an authorized parameter for display in a user profile; (iv) display the sensed biometric parameter on a display screen when the target is within the predetermined range, and (v) remove the sensed biometric parameter from the display screen after the target is outside of the predetermined range.

19. The system of claim 18 wherein the fixed display device is a smart mirror.

20. The system of claim 18 wherein the target is a first target and the fixed display device is further configured to (i) determine that a second target is within the predetermined range of the fixed display device, (ii) receive a second wireless transmission including a second sensed biometric parameter associated with the second target, (iii) display the sensed biometric parameter associated with the second target on the display screen when the second target is within the predetermined range, and (iv) remove the sensed biometric parameter associated with the second target from the display screen after the second target is outside of the predetermined range.

* * * * *